United States Patent
Yamakawa et al.

[11] Patent Number: 6,043,494
[45] Date of Patent: Mar. 28, 2000

[54] GAMMA CAMERA SYSTEM

[75] Inventors: Tsutomu Yamakawa, Tochigi-ken; Takashi Ichihara, Otawara, both of Japan

[73] Assignee: Kabushiki Kaisha Toshiba, Kawasaki, Japan

[21] Appl. No.: 08/857,589

[22] Filed: May 16, 1997

[30] Foreign Application Priority Data

| May 30, 1996 | [JP] | Japan | 8-136291 |
| Nov. 27, 1996 | [JP] | Japan | 8-316119 |
| Nov. 27, 1996 | [JP] | Japan | 8-316307 |

[51] Int. Cl.$^7$ .................................................. G01T 1/161
[52] U.S. Cl. ............................... 250/363.04; 250/363.05; 250/363.09
[58] Field of Search ..................... 250/363.04, 363.05, 250/363.08, 363.09

[56] References Cited

U.S. PATENT DOCUMENTS

| 3,852,601 | 12/1974 | Casale | 250/363.08 |
| 5,155,365 | 10/1992 | Cann et al. | 250/363.04 |
| 5,552,605 | 9/1996 | Arata | 250/363.04 |
| 5,596,197 | 1/1997 | Jones et al. | 250/363.04 |

*Primary Examiner*—Edward P. Westin
*Assistant Examiner*—Richard Hanig
*Attorney, Agent, or Firm*—Oblon, Spivak, McClelland, Maier & Neustadt, P.C.

[57] ABSTRACT

A gamma camera system of the present invention comprises a main detector for detecting gamma rays emitted from RIs provided to a subject, an emitter for emitting the gamma rays to the subject, and a sub-detector for detecting the gamma rays emitted from the emitter and transmitted through the subject. The sub-detector has at least one semiconductor element for directly detecting the gamma ray having high energy resolution. Based on the output of the sub-detector, an absorption ratio showing to what degree the gamma rays are absorbed in the subject is calculated. The absorption ratios are used to correct the number of the gamma rays counted based on the output of the main detector. Based on the corrected count values, RIs distribution is reconstructed. Thus, since the sub-detector having high energy resolution and the emitter other than the main detector are provided, the absorption ratios having high accuracy can be measured in parallel with imaging.

29 Claims, 17 Drawing Sheets

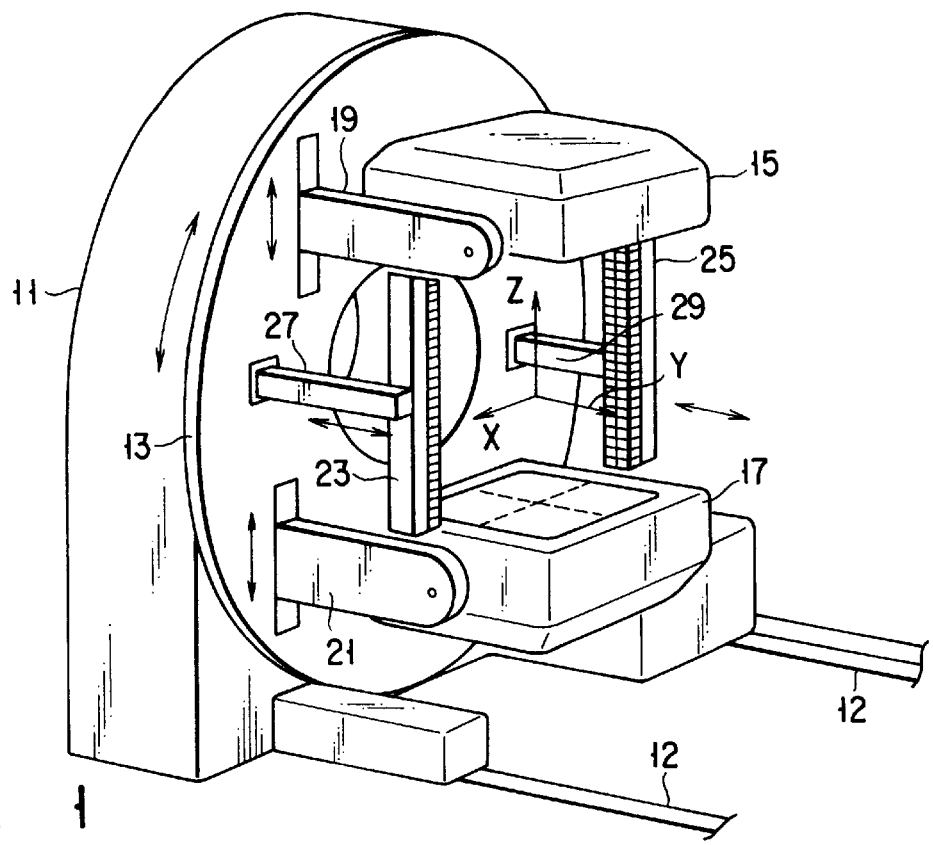
F I G. 1
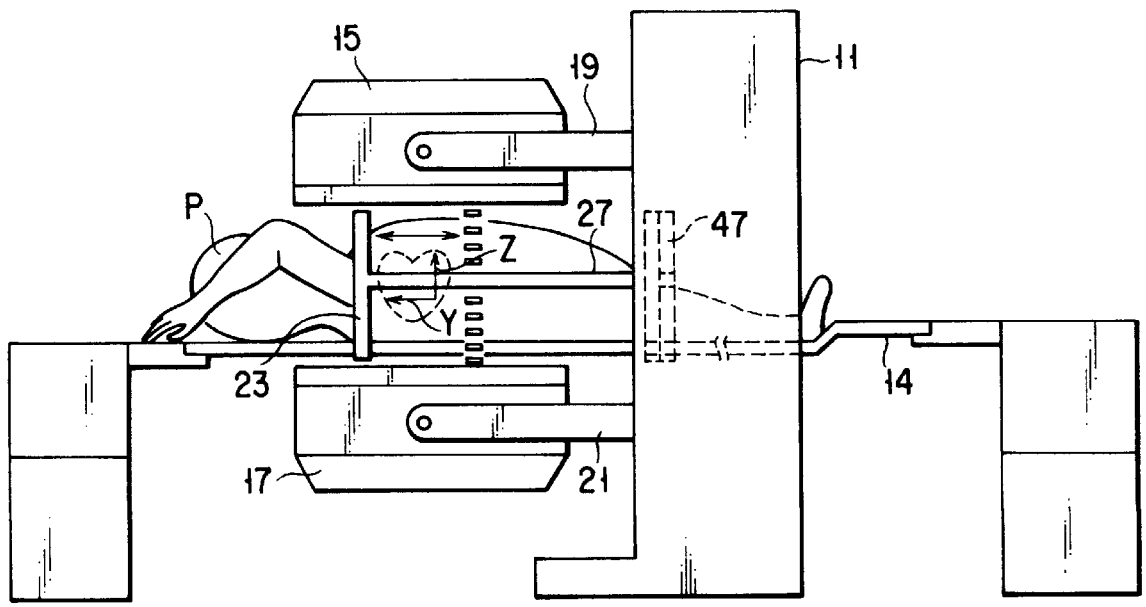
F I G. 2

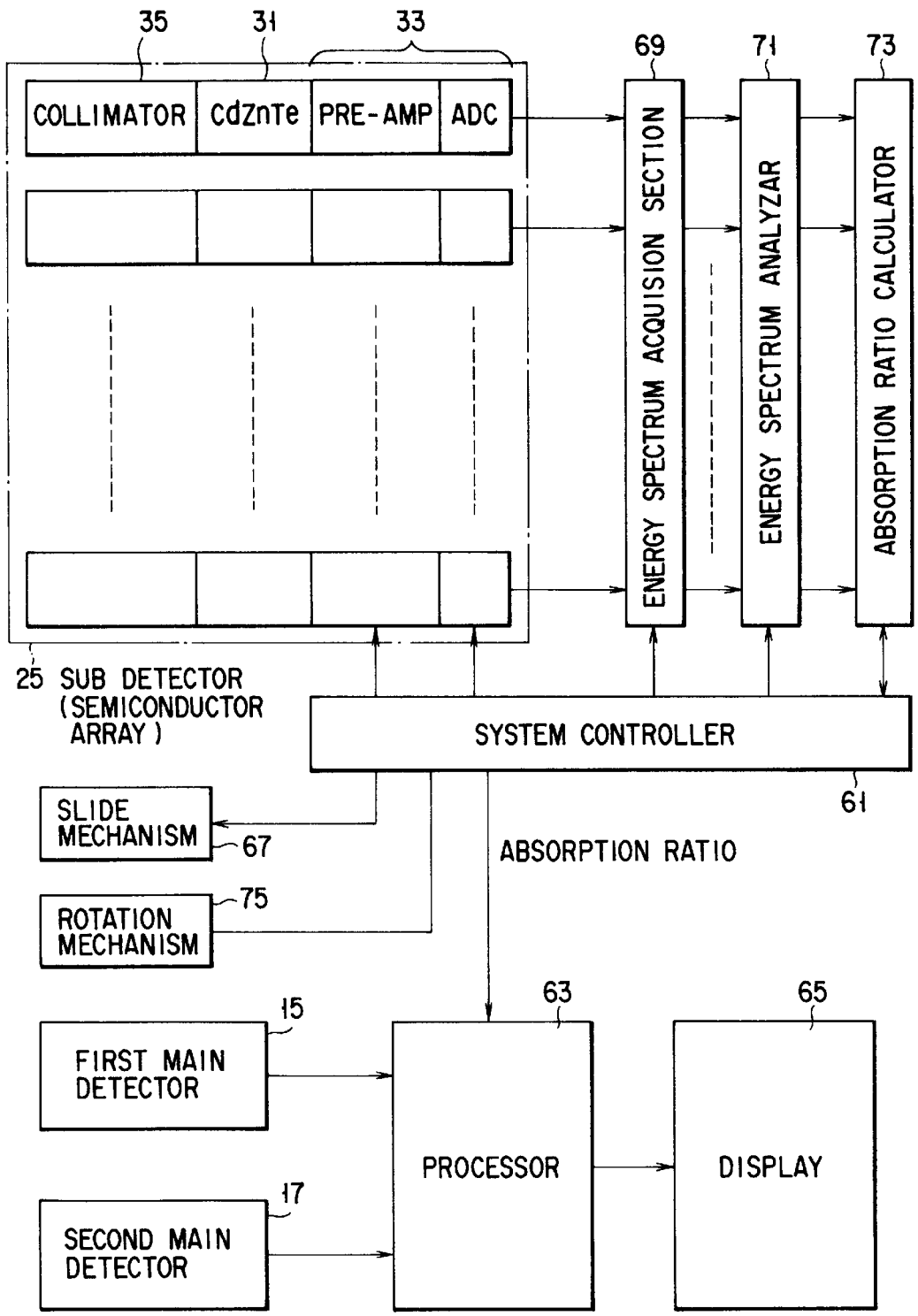
F I G. 12

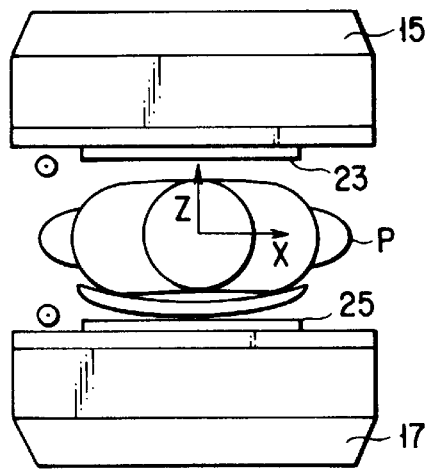
F I G. 15
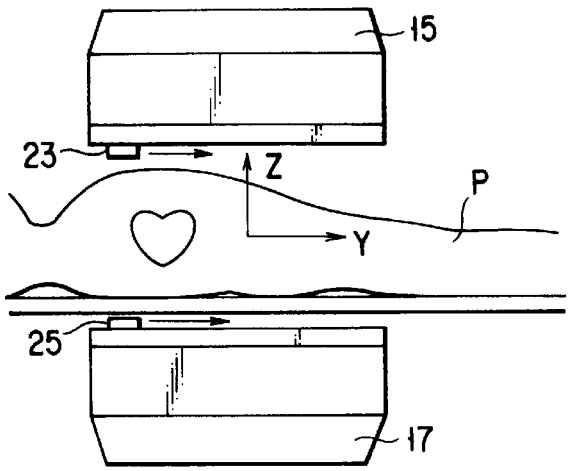
F I G. 16
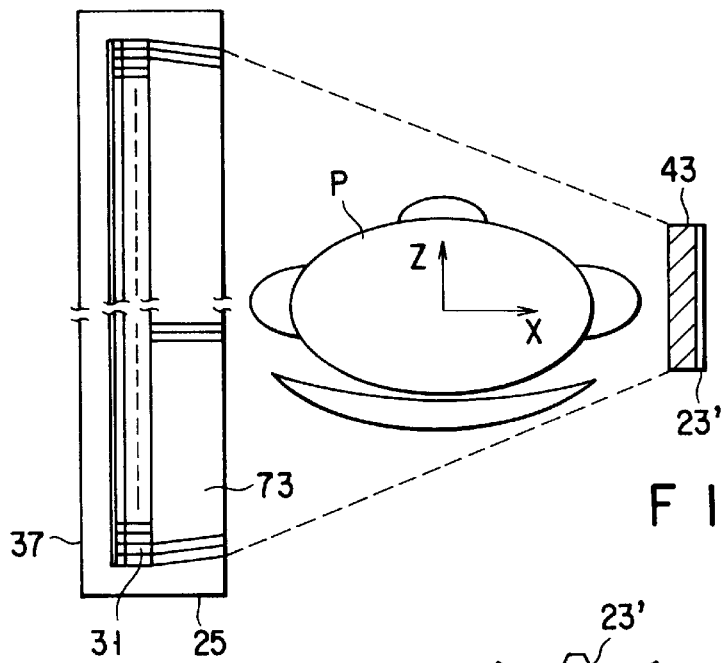
F I G. 17
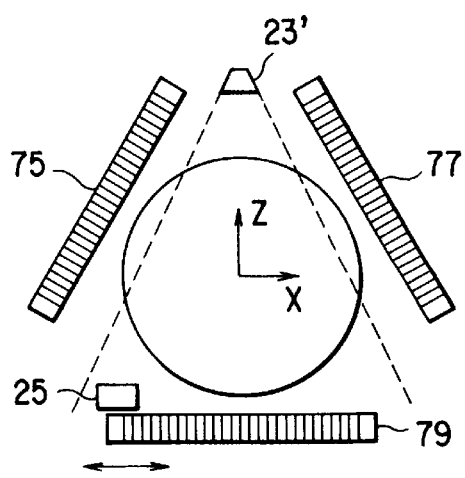
F I G. 18

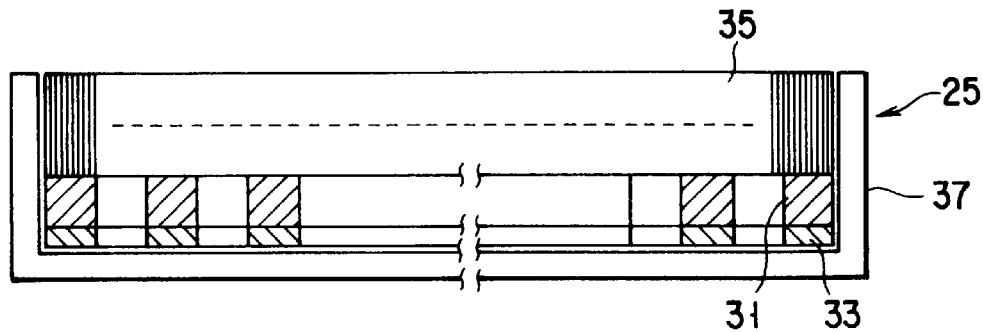
F I G. 22
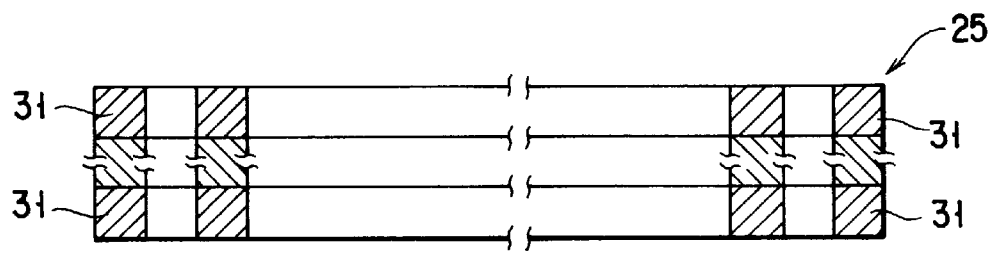
F I G. 23
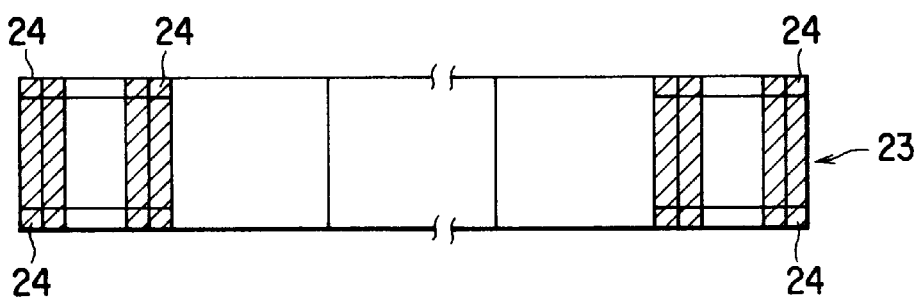
F I G. 24
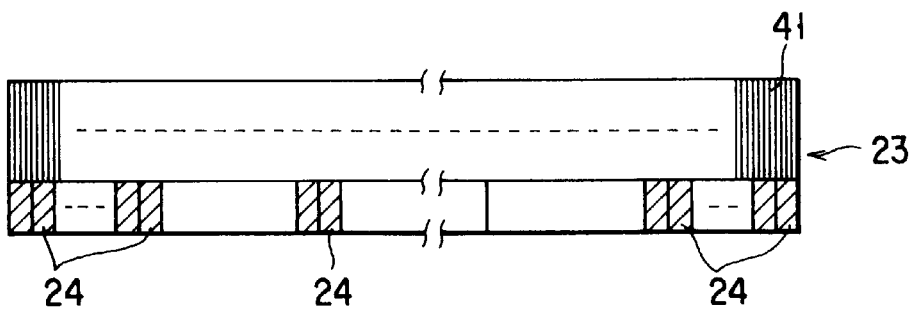
F I G. 25

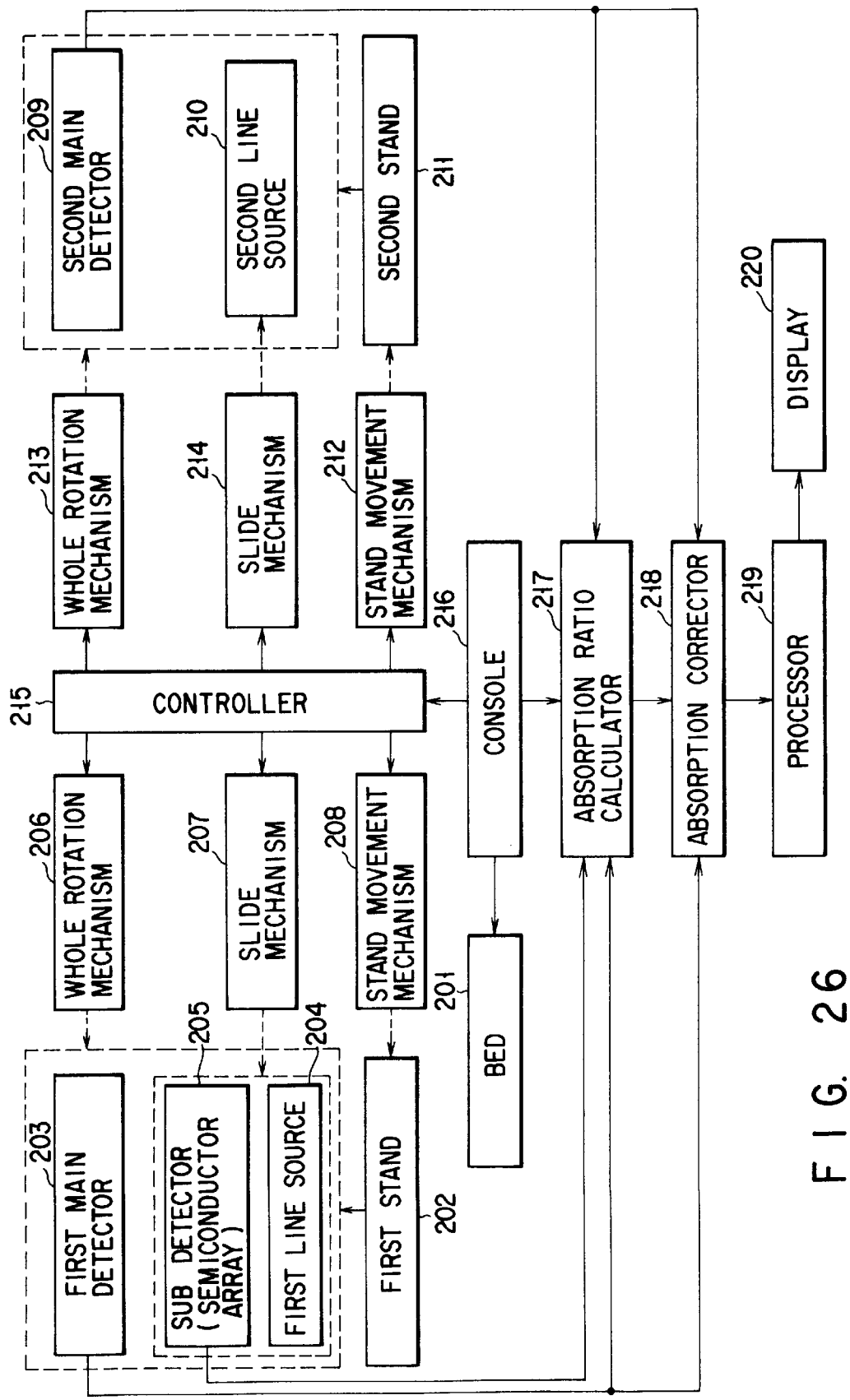
F I G. 26

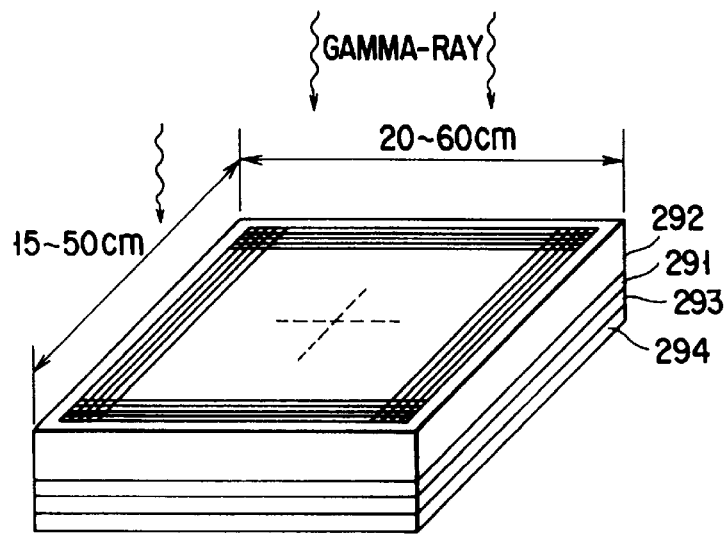
FIG. 27
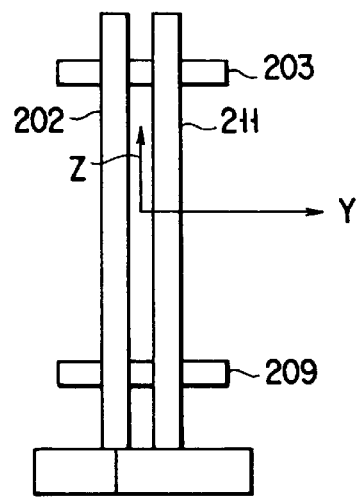
FIG. 31
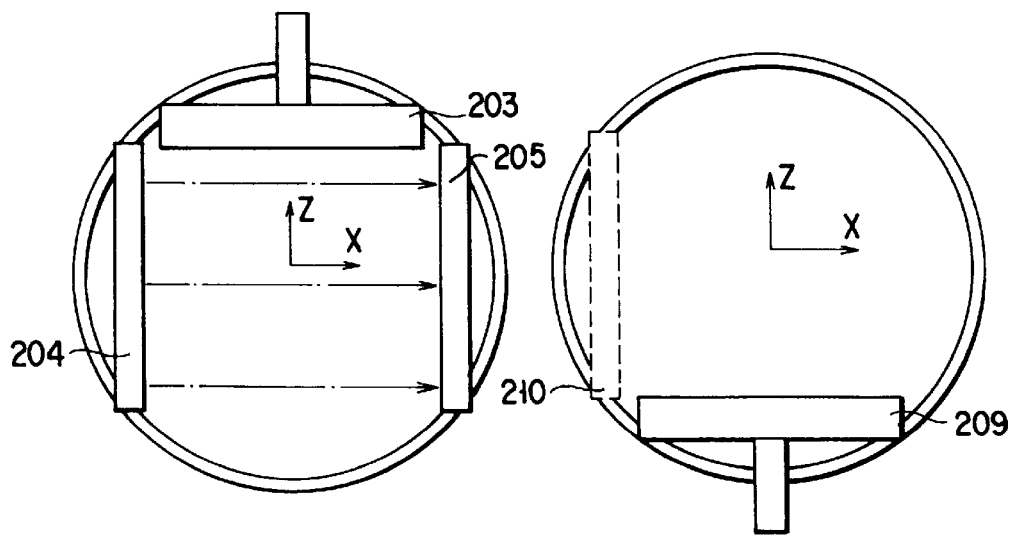
FIG. 32
FIG. 33

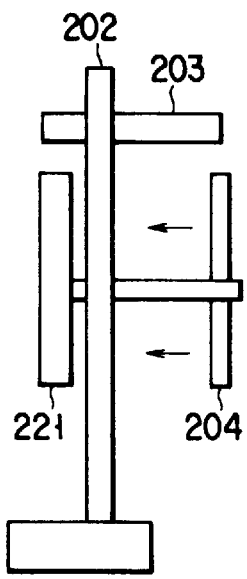
F I G. 34
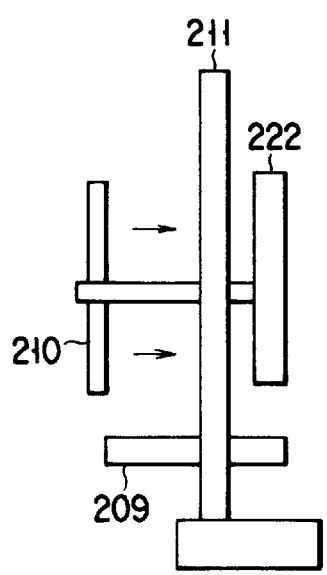
F I G. 35
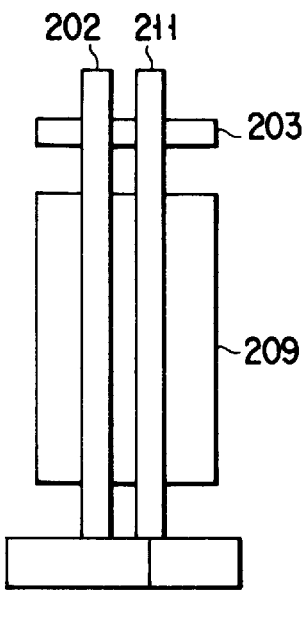
F I G. 36
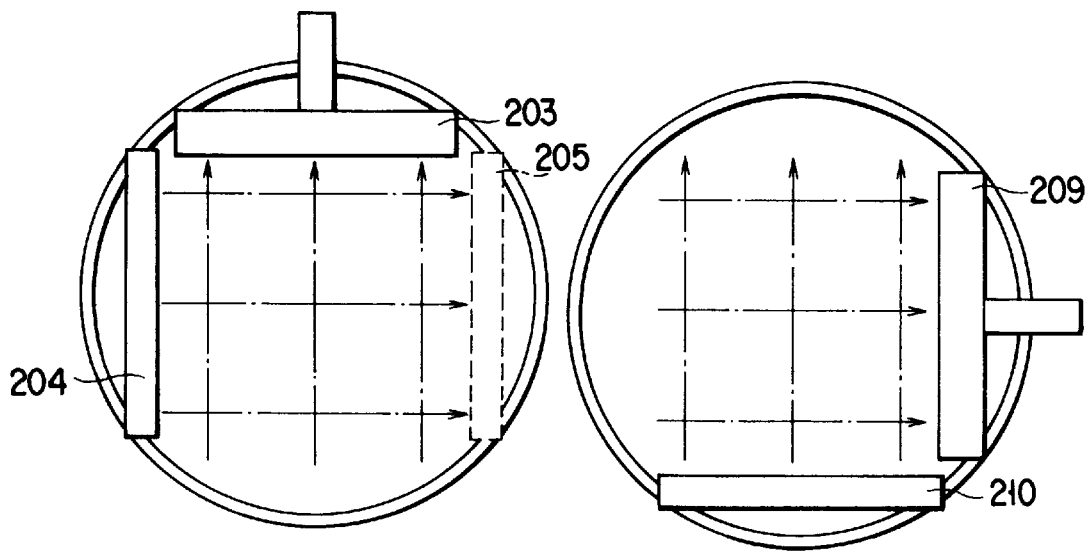
F I G. 37          F I G. 38

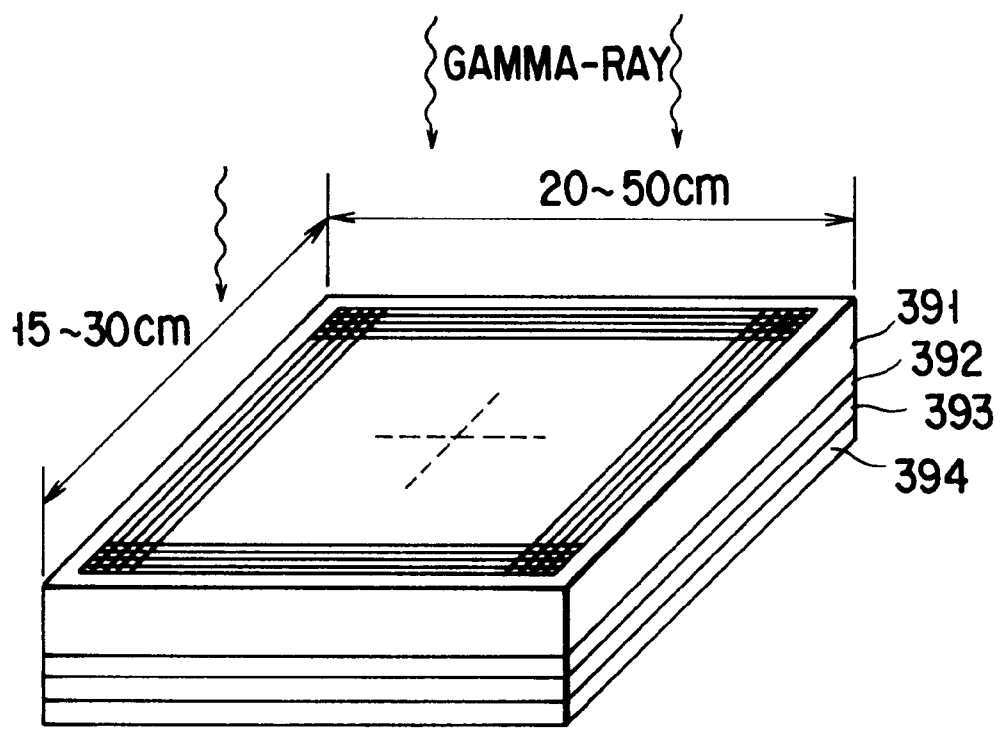
F I G. 40

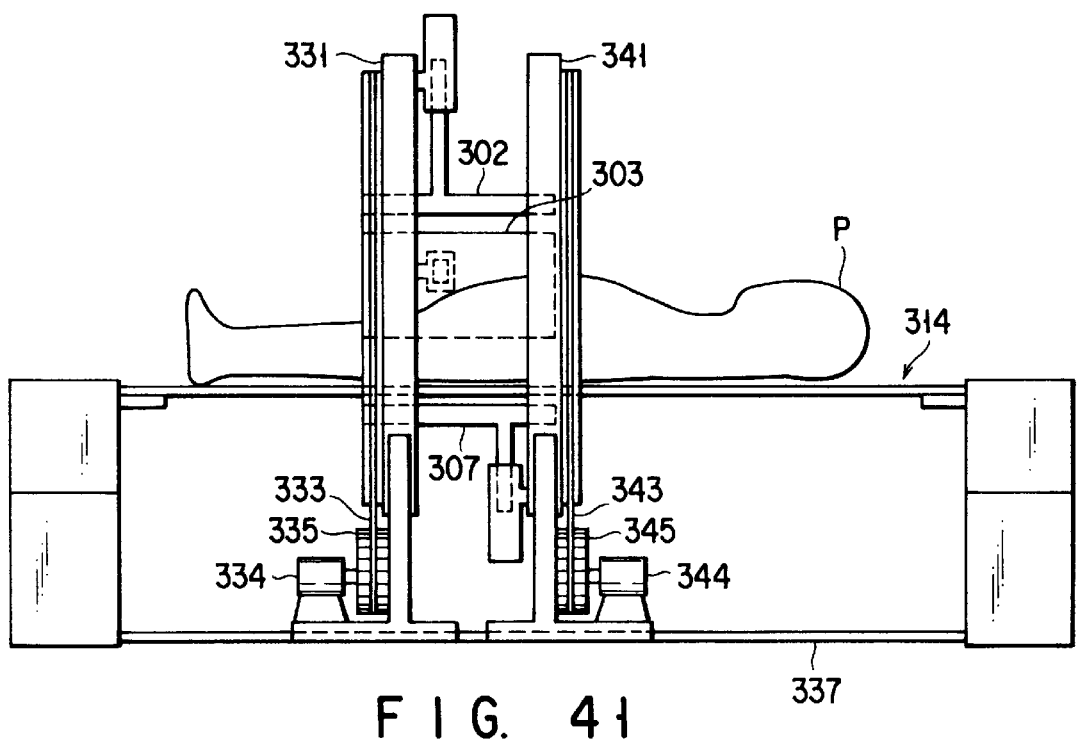
F I G. 41
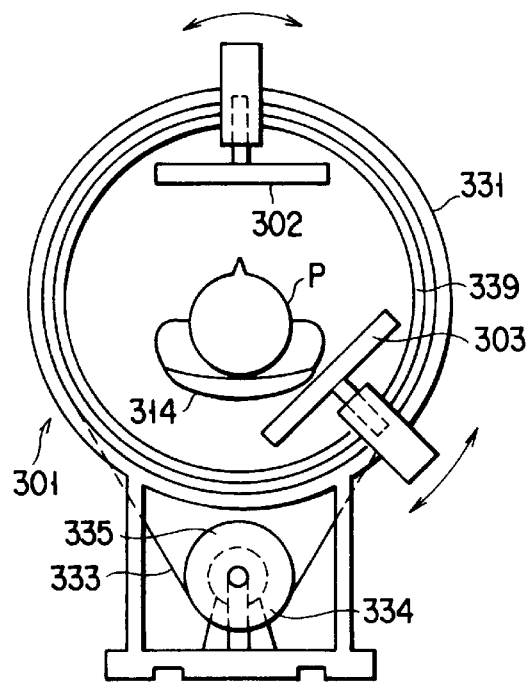
F I G. 42
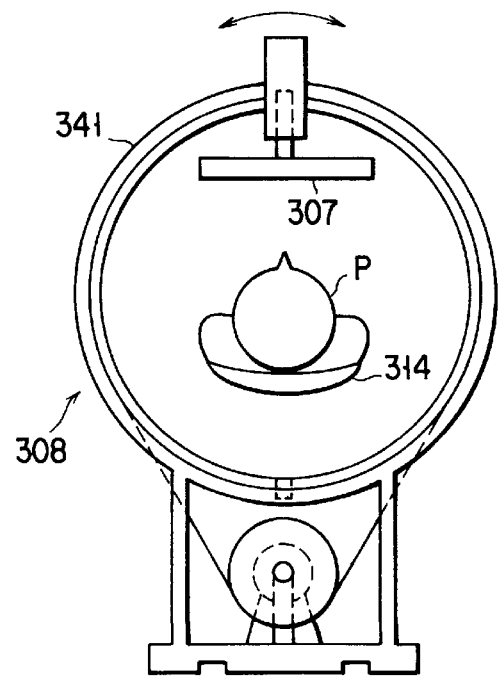
F I G. 43

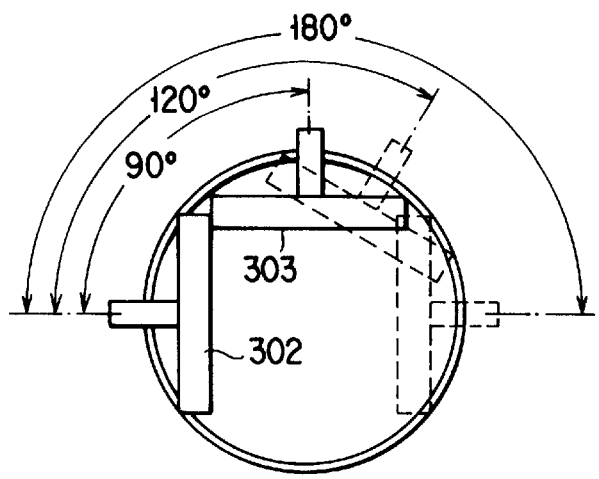
F I G. 44
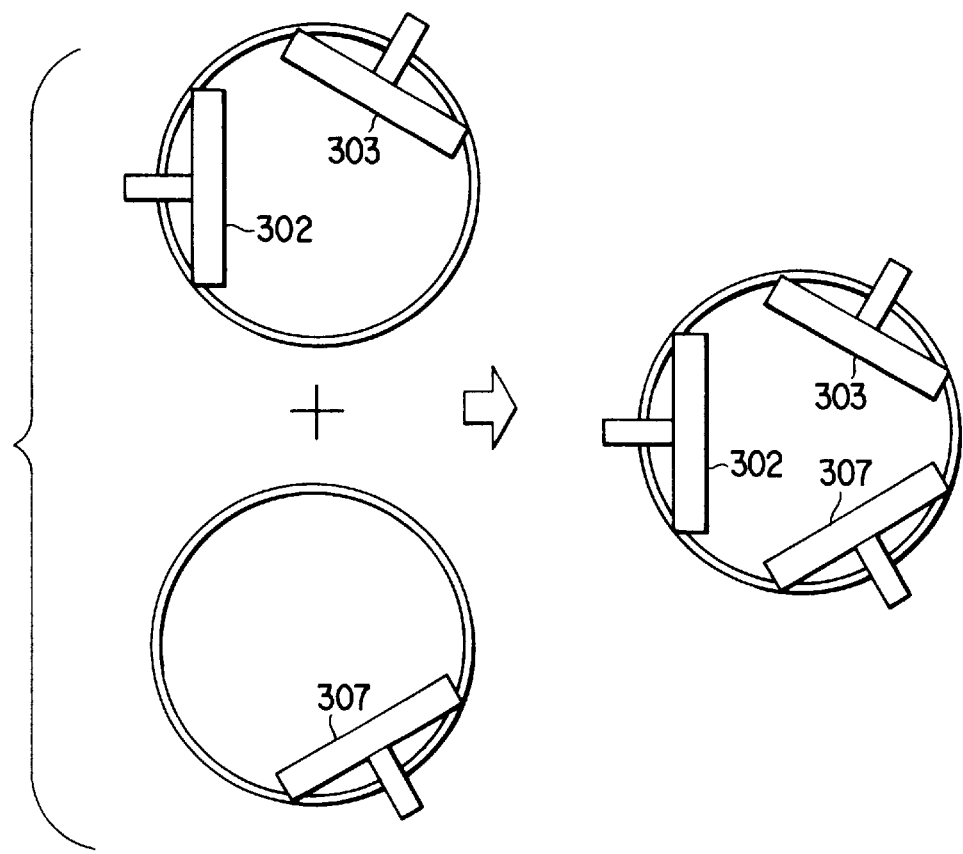
F I G. 45

GAMMA CAMERA SYSTEM

BACKGROUND OF THE INVENTION

The present invention relates to a gamma camera system for detecting gamma rays emitted from radioisotopes (RIs) injected to a subject to image a RI-distribution.

In the gamma camera system, there are two main types. One is a single photon nuclide, which emits one photon at RIs collapse time. The other is a positron nuclide, which inversely emits a pair of photons at a positron disappearing time. The following will explain the general former type.

The main detector of the conventional gamma camera system is an anger-type detector. The anger type detector comprises a collimator for limiting an incident direction of gamma rays, a scintillater for converting the gamma rays to light, a light guide for guiding light, a plurality of photo-electric multipliers (PMTS) for detecting guided light, and a lead shield for shielding disturbance gamma rays.

The anger type detector having a rectangular effective visual field of (35 cm×50 cm) has a size of 55 cm×70 cm×25 cm (thickness), and a weight of over 300 kg. Due to this, a stand and arms were inevitably increased in their sizes and weight to ensure support of such a big and heavy detector.

The gamma camera system has the following kinds of imaging methods:

(Statistic imaging method)

According to this imaging method, the gamma rays are continuously detected for a fixed period of time by the single detector fixed to the subject to obtain the RIs distribution (plane image).

(SPECT imaging method)

According to this imaging method, one detector is rotated around the subject. During the rotation of the detector, the counting of the gamma rays is repeated. Then, the RIs distribution (tomographic image) such as a CAT scan is reconstructed based on the obtained count values of the gamma rays.

(Two-detector opposite SPECT imaging method)

According to this imaging method, two detectors, which are arranged to be opposite to each other, are rotated around the subject. During the rotation of these detectors, the counting of the gamma rays is repeated. Then, a tomographic image such as a CAT scan is reconstructed based on the obtained count values of the gamma rays.

(Three-detector 90° SPECT imaging method)

According to this imaging method, three detectors, which are arranged in a triangular form, are rotated around the subject. During the rotation of these detectors, the counting of the gamma rays is repeated. Then, a tomographic image such as a CAT scan is reconstructed based on the obtained count values of the gamma rays.

In these imaging methods, various kinds of corrections are needed to improve the image quality and the accuracy of a quantitive measurement. For example, there are an energy correction, a linearity correction, a uniformity correction, a scatter correction, a crosstalk correction, an absorption correction, etc. The linearity correction corrects distortion of the peripheral edge of the visual field. The uniformity correction uniforms variations of sensitivity of PMTs. The scatter correction removes a scatter component. The crosstalk correction corrects a crosstalk between two kinds of RIs of different peak energy. The absorption correction corrects a counting error caused by uneven absorption ratios of the organism.

To perform the absorption correction, it is necessary to measure the distribution of the absorption ratios of the subject by use of an emitter in which a radiation frequency of the gamma rays is uniform. The gamma rays emitted from the emitter are sent to the subject. Then, the detector the gamma rays are transmitted through the subject.

If the absorption ratios of the subject are spatially uniformed, the number of incidence of the gamma rays (count values) becomes the same value without depending on the detected position. However, in actuality, since the absorption ratios are not uniformed, the count values depend on the detected position and become uneven.

Therefore, the absorption ratios are obtained, and the count values are multiplied by a reciprocal number of the obtained ratios. As a result, the condition that the absorption ratios are fixed can be satisfied in view of approximation. This is the absorption ratio correction.

However, the absorption correction has the following problems.

(1) The anger-type detector has low energy resolution. The accuracy of the scatter correction or that of the crosstalk correction is reduced by the low energy resolution. The scatter correction with a low accuracy or the crosstalk correction with a low accuracy decreases the accuracy of the absorption correction.

(2) Since both the gamma rays for imaging and the gamma rays for measuring absorption ratios are detected by the anger-type detector, each detection must be operated by an operator. As a result, photographing time was considerably extended.

(3) Since the anger-type detector was so large and heavy, there was a limitation in approaching the detector to the subject. As a result, the measuring accuracy of the absorption ratios was low.

Moreover, the conventional gamma camera system has the following problem.

As mentioned above, since the anger-type detector is so large and heavy, the degree of freedom of the positioning is low. As a result, this kind of gamma camera system cannot correspond to various kinds of imaging, and the specialization of the gamma camera system has advanced.

BRIEF SUMMARY OF THE INVENTION

An object of the present invention is to provide a gamma camera system, which can measure a high accurate absorption ratio in parallel with imaging.

Moreover, an object of the present invention is to provide a gamma camera system, which can flexibly correspond to various kinds of imaging modes, and which can measure a high accurate absorption ratio in parallel with imaging.

A gamma camera system of the present invention comprises a main detector for detecting gamma rays emitted from RIs injected into a subject, an emitter for emitting gamma rays to the subject, and a sub-detector for detecting the gamma rays emitted from the emitter and transmitted through the subject. The sub-detector has at least one semiconductor element for directly detecting the gamma ray having high energy resolution. Based on the output of the sub-detector, an absorption ratio showing to what degree the gamma rays are absorbed in the subject is calculated. The absorption ratios are used to correct the number (count values) of the gamma rays counted based on the output of the main detector. Based on the corrected count values, a RI-distribution is reconstructed. Thus, since the sub-detector having high energy resolution and the emitter other than the main detector are provided, the absorption ratios having high accuracy can be measured in parallel with imaging.

Also, the gamma camera system of the present invention has first and second stands. The first stand has a first main detector for detecting the gamma rays emitted from the RIs injected into the subject, a first emitter for emitting gamma rays, and a sub-detector for detecting the gamma rays emitted from the first emitter and transmitted through the subject. The sub-detector has at least one semiconductor element for directly detecting the gamma rays. The second stand has a second main detector for detecting the gamma rays emitted from the RIs injected into the subject, and a second emitter for emitting gamma rays. These first main detector, the first emitter, the sub-detector, the second main detector, and the second emitter are variously arranged. As a result, the gamma camera system can flexibly correspond to various kinds of imaging modes, and detect a high accurate absorption ratio in parallel with imaging.

Moreover, according to the gamma camera system of the present invention, to detect the gamma rays emitted from the RIs injected into the subject, the first detector having at least one semiconductor element having high energy resolution is supported by the first stand, and the second detector having at least one semiconductor element is supported by the second stand. These first and second detectors are variously arranged. As a result, the gamma camera system can flexibly correspond to various kinds of imaging modes.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a perspective view of a gamma camera system of a first embodiment of the present invention;

FIG. 2 is a side view of the gamma camera system of FIG. 1;

FIG. 12 is a block diagram showing functions of the gamma camera system of the first embodiment of the present invention;

FIG. 15 is a front view showing the line emitter whose position is changed and the semiconductor detector;

FIG. 16 is a side view showing the line emitter of FIG. 15 and the semiconductor detector;

FIG. 17 is a cross-sectional view of the semiconductor detector pairing with the emitter for radically emitting gamma rays;

FIG. 18 is a front view showing a three-detector type;

FIG. 22 is a cross-sectional view of the semiconductor detector having semiconductor elements dispersively arranged;

FIG. 23 is a plane view of the semiconductor detector having semiconductor elements dispersively arranged;

FIG. 24 is a plane view of the line emitter having emitter elements dispersively arranged;

FIG. 25 is a cross-sectional view of the line emitter having emitter elements dispersively arranged;

FIG. 26 is a block diagram showing the functions of the gamma camera system according to a second embodiment of the present invention;

FIG. 27 is a perspective view of the main detector of FIG. 26;

FIG. 31 is a side view showing the main detector of the first photographing system and the main detector of the second photographing system, which is shifted at 180° against the main detector of the first photographing system;

FIG. 32 is a front view of the first photographing system positioned as in FIG. 31;

FIG. 33 is a front view of the second photographing system portioned as in FIG. 31;

FIG. 34 is a side view showing the slide of the line emitter of the first photographing system positioned as in FIG. 31;

FIG. 35 is a side view showing the slide of the line emitter of the second photographing system positioned as in FIG. 31;

FIG. 36 is a view showing the main detector of the first photographing system and the main detector of the second photographing system, which is shifted at 90° against the main detector of the first photographing system, seeing from the side surface;

FIG. 37 is a front view of the first photographing system of positioned as in FIG. 36;

FIG. 38 is a front view of the second photographing system positioned as in FIG. 36;

FIG. 40 is a perspective view of the semiconductor detector of FIG. 39;

FIG. 41 is a side view of the gamma camera system of the third embodiment;

FIG. 42 is a front view of the first photographing system of FIG. 39;

FIG. 43 is a front view of the second photographing system of FIG. 39;

FIG. 44 is a front view showing variations of two semiconductor detectors of the first photographing system of FIG. 39; and FIG. 45 is a front view showing the combination of two semiconductor detectors of the first photographing system of FIG. 39 and one semiconductor detector with the three-detector type.

DETAILED DESCRIPTION OF THE INVENTION

Figure 3:
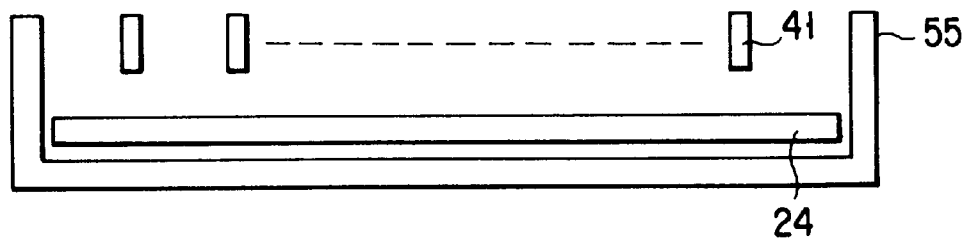
FIG. 3 is a view showing a main detector of FIG. 1, a semiconductor detector, and a line emitter, seeing from the lower portion.

The following will explain embodiments of the present invention with reference to the accompanying drawings. As already explained above, there are two of the gamma camera systems in which one is that a single photon nuclide, which emits one photon at RIs collapse time, is used, and the other is that a positron nuclide, which inversely emits a pair of photons at a positron disappearing time. The following will explain the general former type.

(First embodiment)

FIG. 1 is a perspective view showing the gamma camera system of a first embodiment of the present invention, and FIG. 2 is a side view. In these figures, two main detectors 15 and 17 are anger-type detectors each comprising a collimator, a scintillator, a light guide, a plurality of photo-electric multipliers (PMTs), a lead shield. The collimator limits an incident direction of gamma rays. The scintillator converts the gamma rays, which are passed through the collimator, to light. The light guide guides the converted light. The photoelectric multipliers (PMTs) detects the guided light. The lead shield shields disturbance gamma rays.

These two main detectors 15 and 17 are supported by a stand 11 to be opposite to each other through arms 19 and 21. The arms 19 and 21 are provided on a rotation ring 13. By the rotation ring 13, the main detectors 15 and 17 can be rotated around a subject P.

For convenience, a rotation coordinate system (XYZ) rotating with the rotation of the rotation ring 13 is defined as follows:

A rotation axis is set as a Y-axis, and a line, which connects a center of the detection surface of the main detector 15 to the center of the detection surface of the main detector 17, is set as a Z-axis. At a photographing time, the subject P mounted on a bed 14 is positioned between the main detectors 15 and 17. Generally, the axis of the positioned subject P is substantially consistent with the Y-axis.

On a floor, linear guide rails 12 are provided to be parallel to the Y-axis. The stand 11 is mounted on the guide rail 12. Thereby, the stand 11 can be linearly moved to be parallel to the Y-axis.

The above-mentioned structure is not different from the conventional case. The characteristic point of this embodiment lies in that a line emitter 23 (source) and a sub-detector 25 are provided.

As shown in FIG. 3, the line emitter 23 has a long and rectangular shaped radiation material 24. The radiation material 24 spatially radiates gamma rays at a fixed frequency. The radiation material 24 is contained in a lead case 55 whose only one side is opened. On an opening portion of the case 55, a relatively coarse parallel hole collimator 41 is formed to limit the radiation direction of the gamma rays.

As the radiation material 24, there is selected a material whose energy peak of the gamma rays emitted from the radiation material 24 is different from an energy peak of the gamma rays emitted from RIs given to the subject. The energy peak is defined as energy having the highest radiation frequency of the gamma rays. In such a selection, an energy spectrum, which is collected based on the outputs of the main detectors 15 and 17, is analyzed, thereby making it possible to eliminate an error in which the main detectors 15 and 17 detect the gamma rays emitted from the line emitter 23.

Figure 4:
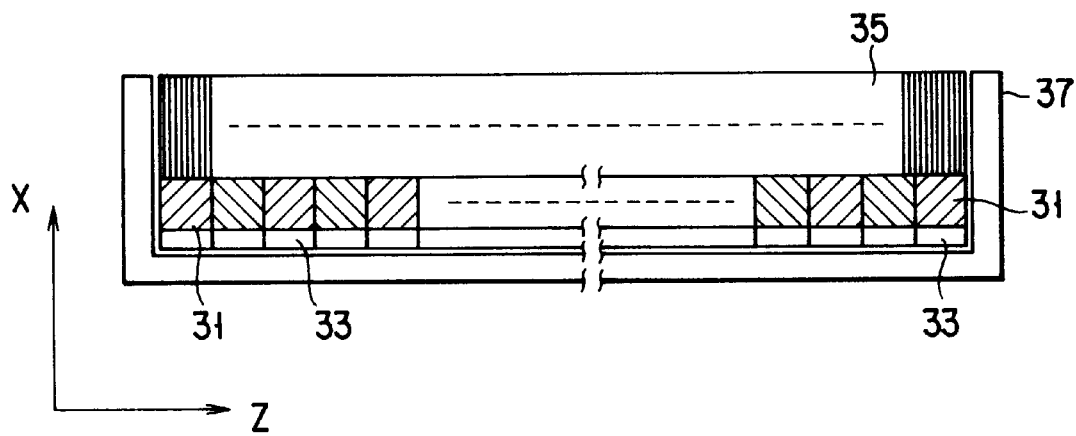
FIG. 4 is a front view showing the main detector of FIG. 1, the semiconductor detector, and the line emitter.
Figure 5:
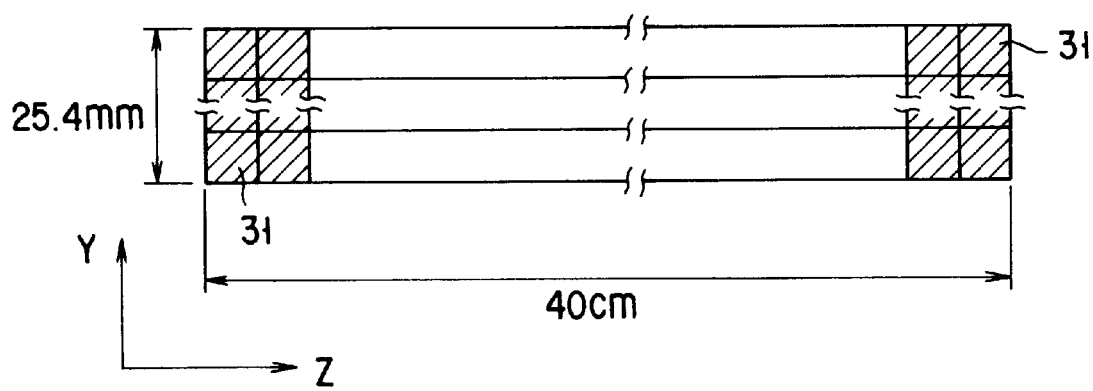
FIG. 5 is a cross-sectional view of the semiconductor detector of FIG. 1.

As shown in FIGS. 4 and 5, the sub-detector 25 has a plurality of semiconductor elements 31, which directly detect the gamma rays to be output as electrical signals. In this principle, a bias voltage is applied to inter-electrodes of the semiconductor elements 31, and the gamma rays are incident onto the semiconductor elements 31. Thereby, an electrical charge moves between the electrodes, so that a current flows to the inter-electrodes. As semiconductor elements 31, for example, CdZnTe is used. The semiconductor elements 31 are arrayed in a matrix form. The matrix approximates to the long and rectangular shape of the radiation material 24.

The matrix of the semiconductor elements 31 is contained in a lead case 37 whose only one side is opened. On an opening portion of the case 37, a relatively close parallel hole collimator 35 is formed to limit the incident direction of the gamma rays.

Also, a circuit board 35 is contained in the lead case 37. On the circuit board 35, a plurality of preamplifiers and a plurality of analog/digital converters are mounted. The preamplifier and the analog/digital converter are prepared to each semiconductor element.

Figure 6:
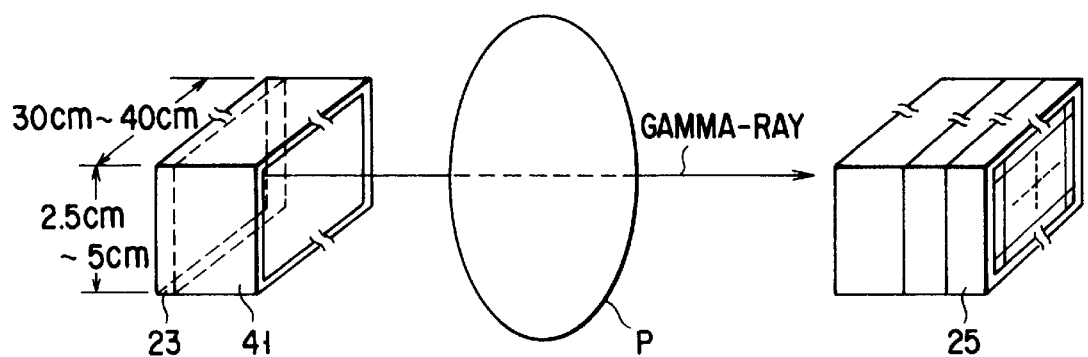
FIG. 6 is a plane view of the semiconductor detector of FIG. 1.

As shown in FIGS. 1 and 2, the line emitter 23 and the sub-detector 25 are supported to be parallel to the z-axis by the stand 11 through arms 27 and 29. As shown in FIG. 6, the line emitter 23 and the sub-detector 25 are positioned to be opposite to each other such that the gamma rays, which are emitted from the line emitter, and which is transmitted through the subject, can be detected by the sub-detector 25.

The arms 27 and 29 are provided on the rotation ring 13 through slide mechanisms 207 and 214. By the rotation of the rotation ring 13, the line emitter 23 and the sub-detector 25 can be rotated around the subject P together with the main detectors 15 and 17. By the slide of the arms 27 and 29, the line emitter 23 and the sub-detector 25 can be slid in a Y-axial direction to scan the subject in the Y-axial direction (direction of the axis of the subject).

Figure 7:
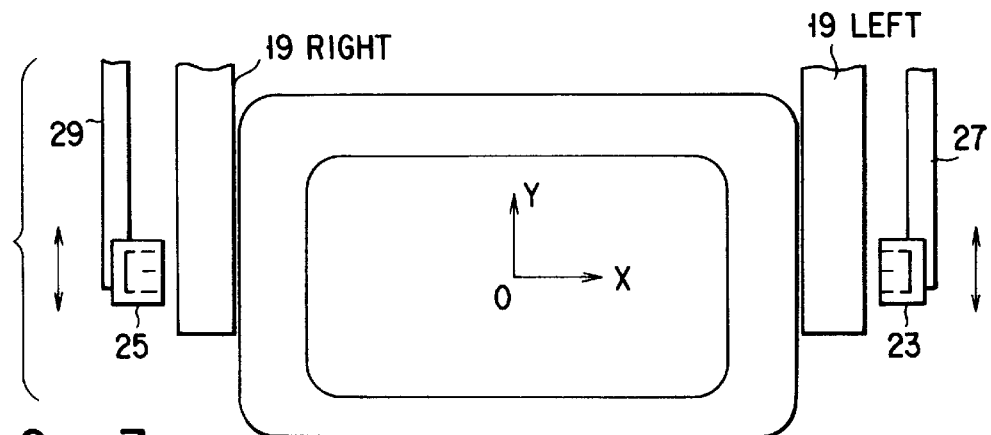
FIG. 7 is a cross-sectional view of the line emitter of FIG. 1.
Figure 8:
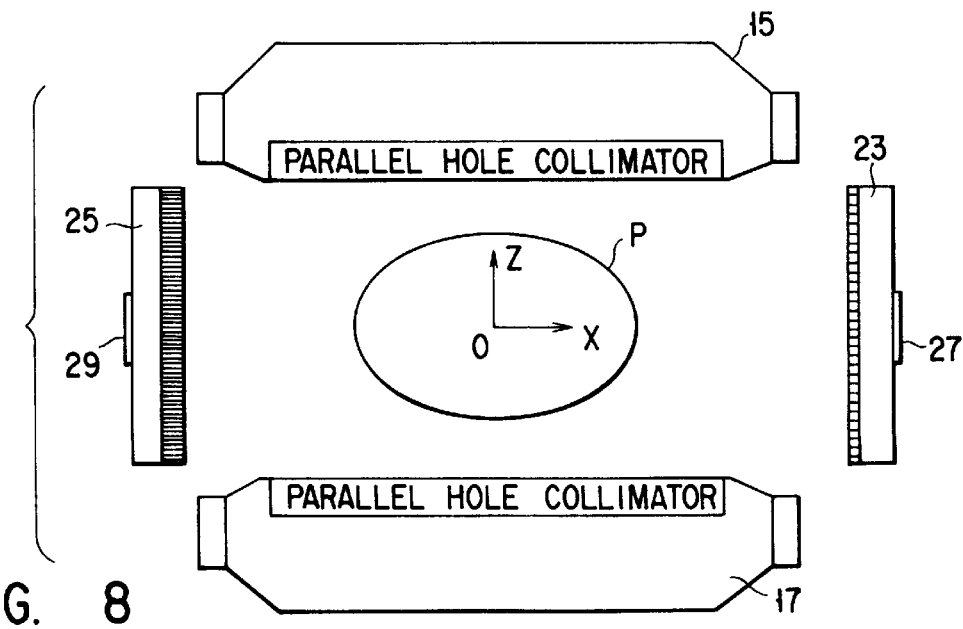
FIG. 8 is a view showing a path of the gamma rays to the semiconductor detector from the line emitter of FIG. 1.

As shown in FIGS. 7 and 8, the line emitter 23 and the sub-detector 25 are arranged in the main detectors 15 and 17 such that the collimated radiation direction of the line emitter 23 and the sub-detector 25 crosses at a right angle with the collimated incident direction of the main detectors 15 and 17. By this arrangement, there can be reduced the frequency of an error generation in which the main detectors 15 and 17 detect the gamma rays emitted from the line emitter 23, that is, the gamma rays emitted from the line emitter 23 pass through the collimator of the main detectors 15 and 17.

Figure 9:
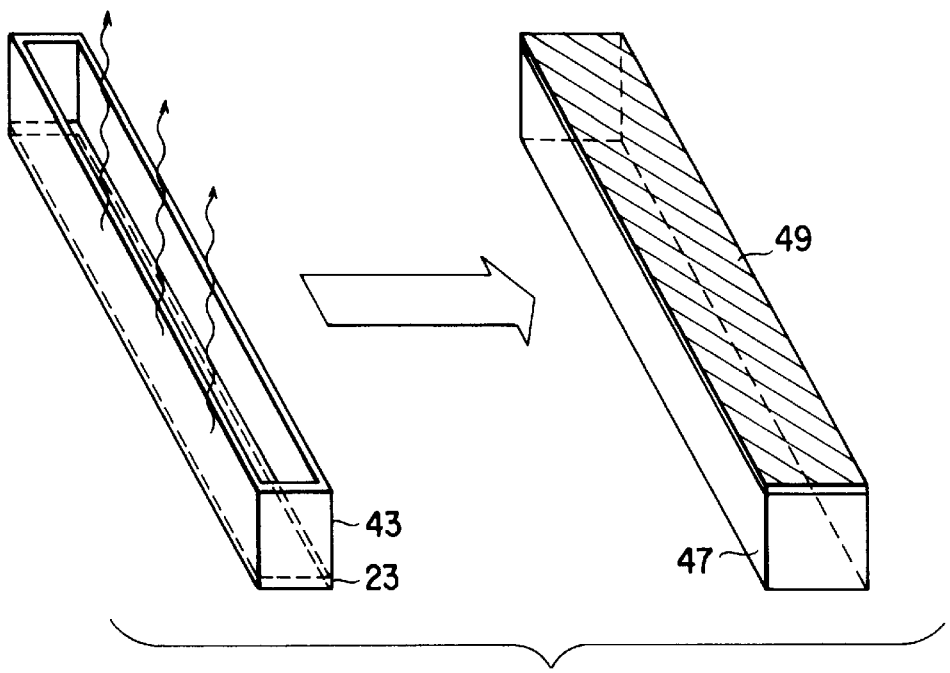
FIG. 9 is a perspective view of a storage of the line emitter of FIG. 1.
Figure 10:
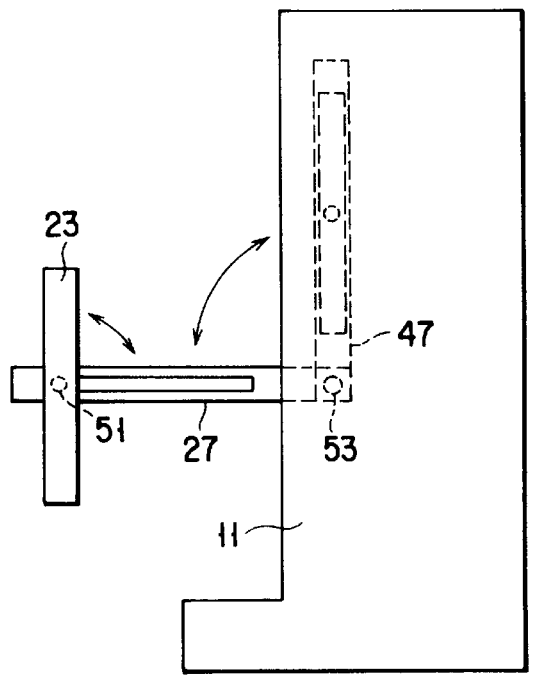
FIG. 10 is a side view of the storage of FIG. 9 and the line emitter.
Figure 11:
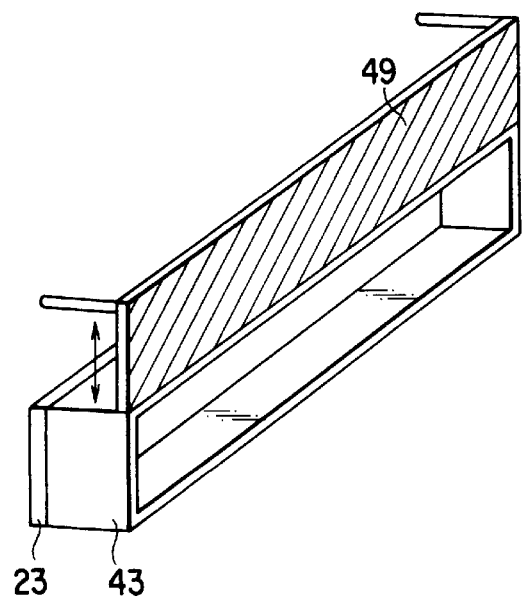
FIG. 11 is a perspective view of a shield cover of the line emitter of FIG. 1.

FIG. 9 shows a storage 47 of the line emitter 23. The line emitter 23 is stored in the storage 47 provided in the stand 11 when it is not used. As shown in FIG. 2, the moved line emitter 23 is stored in the storage 47. Or, as shown in FIG. 10, the line emitter 23 is stored in the storage 47, which is folded by pins 51 and 53. The storage 47 has a lead shield 49 to prevent the gamma rays from being leaked from the stored line emitter 23. As shown in FIG. 11, the shield 49 may be attached to the line emitter 23 in place of the storage 47 to be openable and closable.

FIG. 12 shows a block diagram of the gamma camera system of this embodiment. The gamma camera system has an absorption ratio calculator 73 for calculating absorption ratios based on the output of the sub-detector 25. The absorption ratios are used to reduce an error, which is caused by unevenness of the absorption ratios.

From the line emitter 23, the gamma rays are emitted to the subject at spatially the same frequency. Some of the gamma rays are absorbed in the subject, and the residual gamma rays are transmitted through the subject. The gamma rays transmitted through the subject are made incident to the sub-detector 25.

If the gamma rays are made incident to the semiconductor elements 31, a signal (current signal) is generated. The signal is amplified to be digitized. The signal originally has incident position data of the gamma rays and energy data of the gamma rays. Incident position data is defined by a matrix address of the semiconductor elements 31 to which the signal is output. Energy data is displayed by a current value of the signal.

An energy spectrum acquisition section 69 acquires a plurality of energy spectrums whose incident positions are different based on incident position data and energy data. In the energy spectrums, a horizontal axis shows an energy channel, and a vertical axis shows a number of incidence of the gamma rays (frequency).

The energy spectrum acquisition section 69 has a memory and an address generator. The address generator generates an address signal in accordance with an incident position (YZ) and energy. When the address signal is generated, the address value is incremented by one in the memory. If such a counting is continued for a fixed period of time, the plurality of the energy spectrums whose incident positions are different are acquired.

An energy spectrum analyzer 71 removes each of a scatter component and a crosstalk component from the energy spectrums in accordance with the well-known method (scatter correction and crosstalk correction).

The absorption ratio calculator 73 calculates an absorption ratio for each incident position based on the energy spectrums in which the scatter correction and the crosstalk correction are made. The absorption ratio shows a ratio of the number of emitted gamma rays to the number of the passed gamma rays. For example, it is assumed that 100 gamma rays are emitted and 80 gamma rays thereamong are transmitted. In this case, an absorption ratio is expressed by 80/100=0.8.

Data of the absorption ratio is sent to a processor 63 through a system controller 61 to be used as an absorption correction. The processor 63 counts the incident gamma rays for each incident position based on the outputs of the main detectors 15 and 17. The processor 63 multiplies the counted value (number of the incident gamma rays) by a reciprocal number of the absorption ratios (absorption correction). By this multiplication, the variations of the count values, which depend on the unevenness of the absorption ratios, can be reduced. Then, the processor 63 reconstructs a RIs distribution (plane image or tomographic image) based on the absorption-corrected count values. The RIs distribution is displayed on a display 5.

As shown in FIG. 12, a slide mechanism 67 has a structure, which is necessary to slide the line emitter 23 and the sub-detector 25 to be parallel to the Y-axis, and a stepping motor, etc. A rotation mechanism 75 has the rotation ring 13 and the stopping motor etc., to rotate the main detectors 15 and 17 and the sub-detector 25 around the subject.

The rotations of the main detectors 15 and 17, the line emitter 23, and the sub-detector 25, and the slide of the line emitter 23 and the sub-detector 25 are each controlled by the system controller 61. In a SPECT imagining, for example, a rotation of 5° and a rotation stop for a predetermined period of time are alternately repeated. During the rotation stopping period, the gamma rays from RIs provided onto the subject are continuously detected by the main detectors 15 and 17.

Also, during the rotation stopping period, the line emitter 23 and the sub-detector 25 slide from an end to an end of an effective visual field of the main detectors 15 and 17 (from and end to an end of a photographing portion of a heart, etc.) at a fixed speed. During a next rotation stopping period, the line emitter 23 and the sub-detector 25 inversely slide in the same distance at the same speed.

During the sliding, the gamma rays, which are emitted from the line emitter 23 and transmitted through the subject, are continuously detected by the sub-detector 25, so that the energy spectrums are acquired. Then, as mentioned above, the absorption ratios are calculated based on the energy spectrum.

As explained above, according to this embodiment, the absorption ratios can be obtained by the line emitter 23 and the sub-detector 25 in parallel with the main photographing operation using the main detectors 15 and 17.

Figure 13:
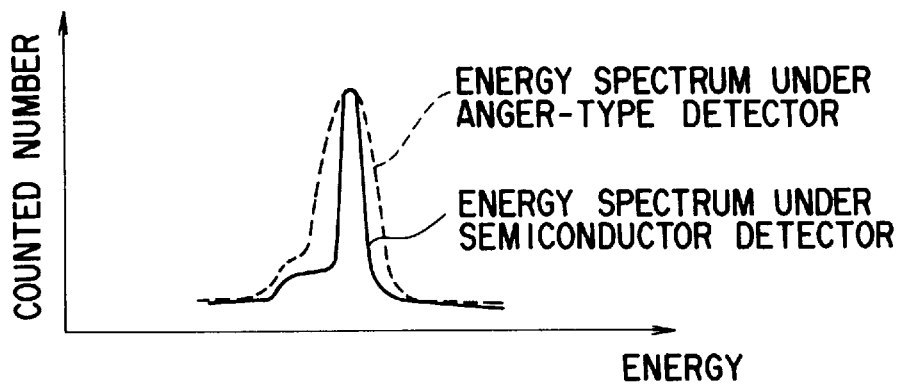
FIG. 13 is a comparison view between energy resolution of the anger-type detector and that of a semiconductor detector.

As shown in FIG. 13, the sub-detector 25 has considerably higher energy resolution than the conventional anger-type detector for the following reason:

Specifically, in the sub-detector 25 using the semiconductor elements, the detection efficiency of gamma ray is higher than the anger-type detector using the scintillator or PMTs. In other words, energy loss at the detection time is small. The anger-type once converts the gamma rays to light to be detected. The semiconductor detector can directly detect the gamma rays as electrical signals. Moreover, in the anger-type detector, the signal components of a plurality of gamma rays, which are made incident at the same time, are mixed to be output as signals. As a result, there is difficulty in separating the respective signal components. In the semiconductor detector, even if the plurality of gamma rays is made incident at the same time, each of these gamma rays is detected by a different semiconductor element to be output as a signal. As a result, there is originally no problem of the mixture of the signal components.

The above-explained embodiment can realize the following technical advantages:

(1) In a conventional case, the absorption ratios were obtained by use of the main detector. Due to this, the absorption ratios were not able to measure in parallel with the SPECT imaging, or there was difficulty in measuring the absorption ratios in parallel with SPECT imaging. However, in the above-explained embodiment, since the line emitter and the sub-detector are added to measure the absorption ratios, the absorption ratios can be easily measured in parallel with the SPECT imaging.

(2) Since the line emitter and the sub-detector are line-shaped, the subject is little subjected to an oppressive feeling. Also, a working space can be widely obtained. The amount of using expensive radiation materials and the semiconductor elements can be kept to a minimum. In this case, since the line emitter and the sub-detector detect the transmitted gamma rays as being slid to measure the absorption ratios, the measuring time is reduced. However, a measuring error due to the time reduction can be compensated with high energy resolution of the semiconductor element.

(3) The emitting direction of the line emitter and the incident direction of the main detector are substantially perpendicular to each other. As a result, there can be restrained the generation of an error in which the main detectors 15 and 17 detect the gamma rays emitted from the line emitter 23.

(4) As the radiation material 24, there is selected a material whose energy peak of the gamma rays emitted from the radiation material 24 is different from an energy peak of the gamma rays emitted from RIs given to the subject. As a result, the above error generation can be eliminated by energy spectrum analysis using the processor.

(5) Even in the head SPECT, the heart SPECT, or the other SPECT, the absorption correction can be performed by the same method.

(6) Even if the SPECT acquisition mode is a continuous acquisition an SPECT acquisition, or a latest close orbit acquisition, the absorption correction can be performed.

(7) When no absorption correction is performed, the line emitter and the sub-detector are withdrawn from the subject to shield or detach the line emitter. Thereby, safety against the gamma rays to which the subject and an operator in an examination room are subjected can be easily ensured.

Figure 14:
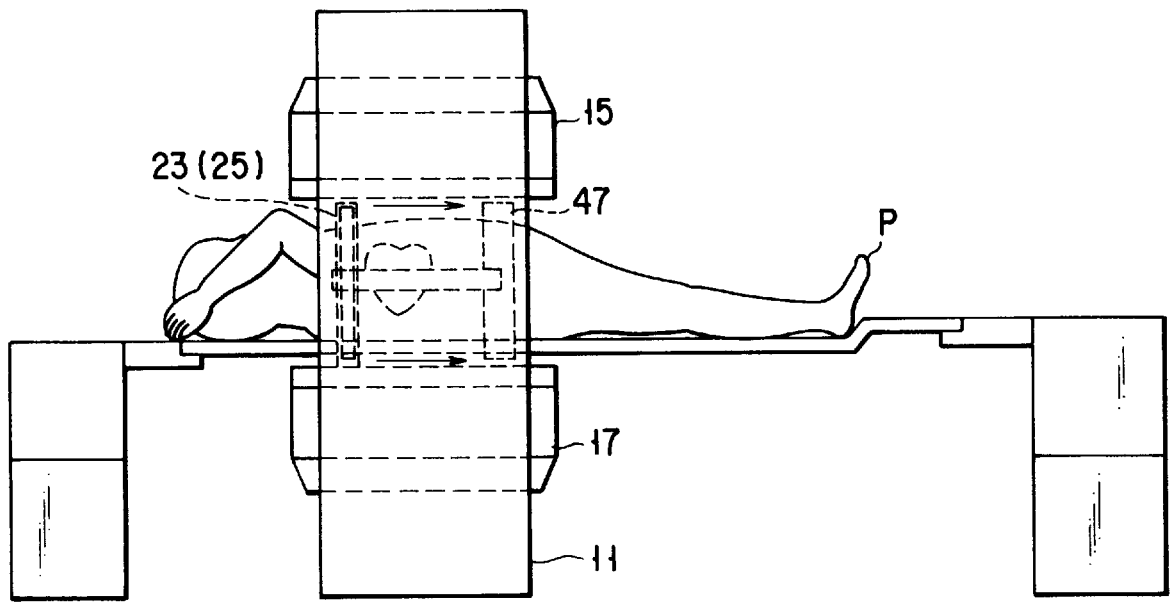
FIG. 14 is a side view of a main detector built-in type.

(8) As shown in FIG. 14, even in the type in which the main detectors 15 and 17 are built in the stand 11, the line emitter 23 and the sub-detector 25 can be incorporated into the stand 11.

The following will explain the modifications of the above-explained embodiment.

More specifically, in the above embodiment, the line emitter 23 and the semiconductor detector 25 were arranged to be parallel to the Z-axis to be slid in parallel with the Y-axis. However, the line emitter 23 and the semiconductor detector 25 may be arranged to be parallel to the Y-axis to be slid in parallel with the Z-axis.

Also, as shown in FIGS. 15 and 16, the line emitter 23 and the semiconductor detector 25 may be arranged to be parallel to the X-axis on the detecting surfaces of the main detectors 15 and 17 to be slid in parallel with the Y-axis.

Moreover, as shown in FIG. 17, a fan beam type collimator may be attached to the line emitter 23 and the sub-detector 25. This can improve spatial resolution in the measurement of the absorption ratios, and is particularly useful to a relatively small sized subject such as small children, small animals, a head portion, etc.

As shown in FIG. 18, this embodiment can be applied to a device, which is dedicated to SPECT in which three main detectors 75, 77, 79 are arranged in a triangular form. In this case, the line emitter 23 is positioned at the vertex of a triangle, and the sub-detector 25 is slidably positioned on the detecting surface of the main detector 79, which is opposite to the line emitter 23.

Figure 19:
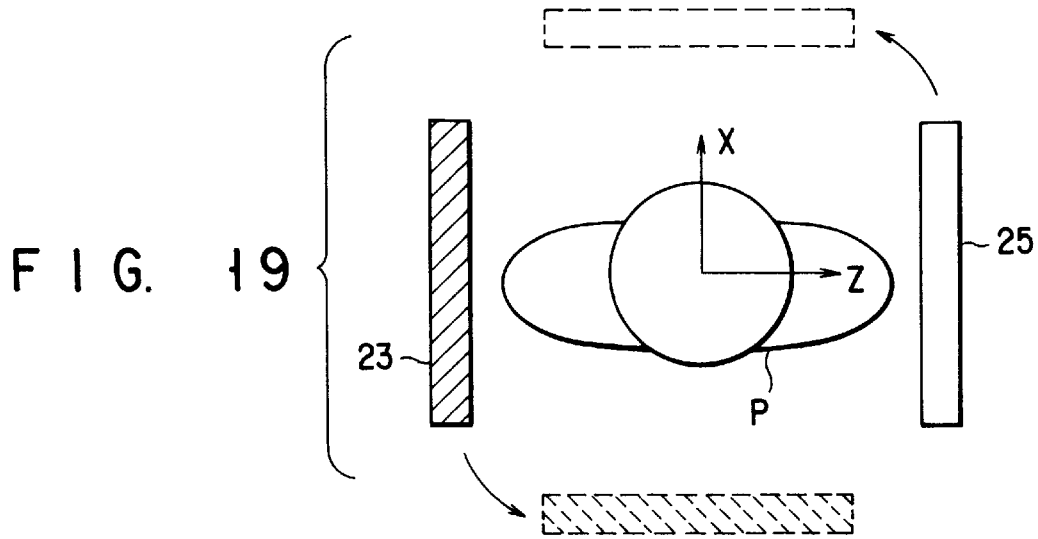
FIG. 19 is a view showing the line emitter rotating with the main detector and the movement of the semiconductor detector.

Moreover, as shown in FIG. 19, the distribution of the absorption ratios of the gamma rays or the RIs distribution can be reconstructed by the processor based on the output of the sub-detector 25.

Figure 20:
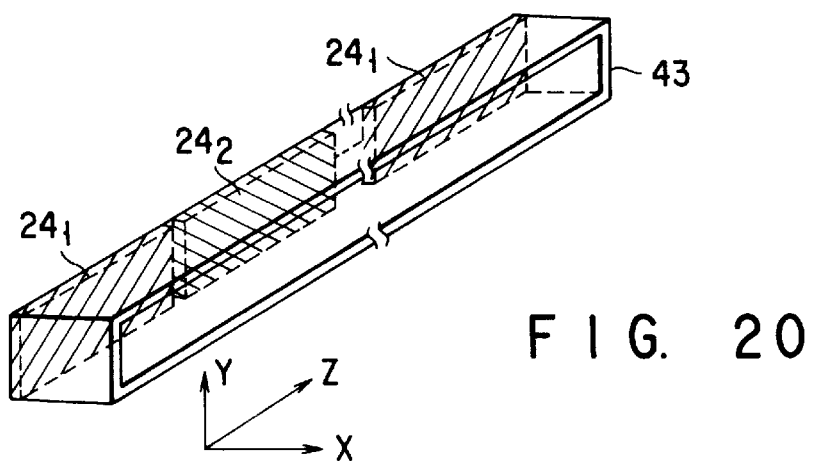
FIG. 20 is a perspective view showing the line emitter for radiating two kinds of gamma rays.
Figure 21:
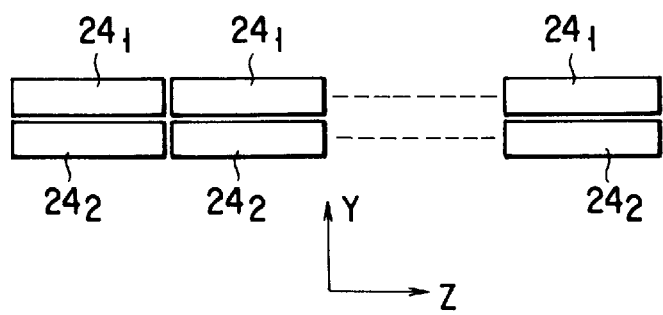
FIG. 21 is a plane view showing the other line emitter for radiating two kinds of gamma rays.

As line emitter 23, as shown in FIG. 20, two kinds of radiation materials 241 and 242, that is, $^{57}Co$ and $^{241}Am$ whose peak energy is different from each other are alternatively arranged. Or, the array of the radiation materials 241 and that of the radiation materials 242 are arranged to be parallel to each other. Thereby, two kinds of gamma rays may be selectively emitted.

The count values (emission data) of the gamma rays, which are emitted from RIs detected by the sub-detector 25, and the count values (transmission data) of the gamma rays, which are emitted from the line emitter 23 and transmitted through the subject, are separated by the energy spectrum analysis based on the difference in peak energy. As a result, emission data may be used to reconstruct the RIs distribution. The method of obtaining the RIs distribution, which is based on the emission count values on basis of the output of the sub-detector 25, and the count values of the main detector 15, is useful to a case when the sub-detector 25 slides on the entire detecting surface of the main detector 15 as shown in FIGS. 15 and 16.

A shown in FIGS. 22 and 23, the semiconductor elements 31 may be dispersively arrayed. Also, as shown in FIGS. 24 and 15, the radiation materials 24 of the line emitter 23 may be dispersively arrayed. In this case, in the slide mechanism 67 for sliding the sub-detector 23 or the line emitter 23, there is provided a function of rocking the sub-detector 25 or the line emitter 23. Thereby, the same function as the case in which the emitters 24 are closely and continuously arranged.

(Second embodiment)

Figure 28:
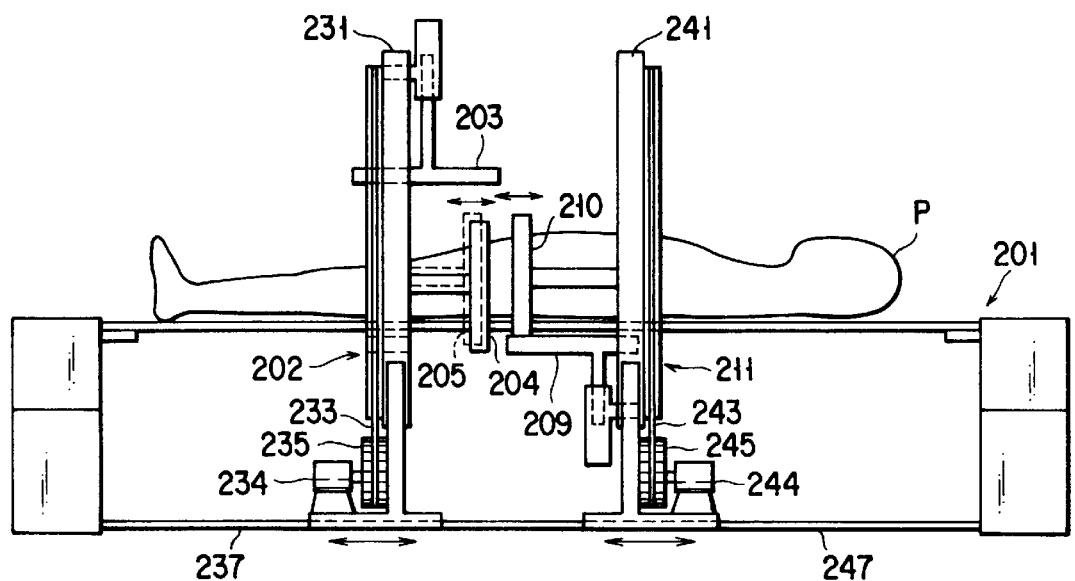
FIG. 28 is a side view of the gamma camera system of FIG. 26.
Figures 29, 30:
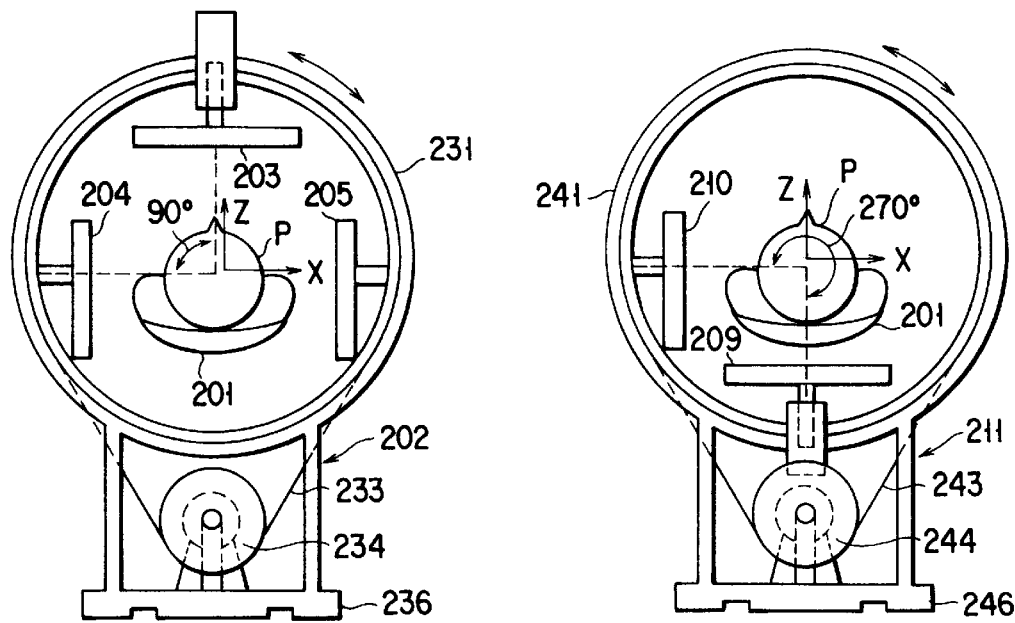
FIG. 29 is a front view of a first photographing system of FIG. 1.
FIG. 30 is a front view of a second photographing system of FIG. 1.

FIG. 26 shows a block diagram of the gamma camera system of a second embodiment. FIG. 28 shows the side view of the gamma camera system. FIGS. 29 and 30 show front views of first and second imaging systems, respectively. An object of this embodiment is to provide a gamma camera system, which can flexibly correspond to various kinds of imaging modes, and which can measure the absorption ratios with high accuracy in parallel with imaging. Due to this, the system of this embodiment comprises two imaging systems, which are physically separated from each other.

A first imaging system has a first main detector 203. The first main detector 203 is a semiconductor detector as shown in FIG. 27. The semiconductor detector comprises a semiconductor array 291, a collimator 292, a circuit board 293, and a lead shield 294. In the semiconductor array 291, a plurality of semiconductor elements (CdZnTe), which directly detect the gamma rays, are arrayed in a matrix manner. The collimator 292 limits the incident direction of the gamma rays to the semiconductor array 291. The circuit board 293 has a preamplifier, a read-out circuit, etc., mounted thereon. The lead shield 294 shields disturbance gamma rays. This detector has the size of 15 to 50 cm×20 to 60 cm.

The first main detector 203 is supported by a rotation ring 231 of a first stand 202 to be rotatable around the subject P mounted on a bed 201. The rotation axis of the rotation ring 231 is consistent with the Y-axis. The first stand 202 is mounted on a rail 247 provided on the floor. Thereby, the first stand 202 can be slid to be parallel with the Y-axis.

In the rotation ring 231, a first line emitter 204 is supported. As a radiation material of the first line emitter 204, there is selected a material whose energy peak of the gamma ray is clearly different from the energy peak of the gamma ray emitted from RIs given to the subject.

The first line emitter 204 is shifted at substantially 90° against the first main detector 203 in connection with the rotation axis. Also, in the rotation ring 231, a sub-detector 205 is supported to be opposite to the first line emitter 204.

A whole rotation mechanism 206 comprises the rotation ring 231, a stepping motor 234, a pulley 235, and a driving belt 233. Similar to the first embodiment, the first line emitter 204 and the sub-detector 205 slide along the Y axis to scan the subject. This can be realized by a slide mechanism 207.

A second imaging system has a second main detector 209. The second main detector 209 is also a semiconductor detector. The second main detector 209 is supported by a rotation ring 241 of a second stand 211 to be rotatable around the subject P mounted on the bed 201. The second stand 211 is mounted on the rail 247 sharing with the first stand 202 such that the rotation axis of the rotation ring 241 is consistent with the rotation axis 231 of the first system.

In the rotation ring 241, a second line emitter 210 is supported. As a radiation material of the second line emitter 210, there is selected a material whose energy peak of the gamma ray is clearly different from the energy peak of the gamma ray emitted from RIs given to the subject.

The second line emitter 210 is shifted at substantially 270° against the second main detector 209 in connection with the rotation axis. Unlike the first imaging system, a sub-detector is not provided in the second imaging system.

A whole rotation mechanism 123 comprises the rotation ring 241, a stepping motor 244, a pulley 245, and a driving belt 243. The second line emitter 210 slides along the Y axis. This can be realized by a slide mechanism 214.

A controller 215 relatively controls the movement of the first and second imaging systems to flexibly correspond to the various kinds of imaging modes.

An absorption ratio calculator 217 selects the output of the first main detector 203, that of the second main detector 209, and that of the sub-detector 205 in accordance with the imaging mode. Then, the absorption ratio calculator 217 calculates the absorption ratios based on the selected outputs. Since this calculation is the same as the first embodiment, the explanation will be omitted.

An absorption corrector 218 counts the output of the first main detector 203 and/or the output of the second main detector 209, and multiplies the counted value by a reciprocal number of the absorption ratios (absorption correction). A processor 219 reconstructs the RIs distribution (plane image or tomographic image) based on the count values, which is absorption-corrected by the absorption corrector 218. A display 220 displays the RIs distribution reconstructed by the processor 219.

The above-structured embodiment can correspond to the following various kinds of imaging modes by combining two imaging systems, which are physically separated from each other.

(Static image)

In this mode, at least one of two main detectors 203 and 209 is used to reconstruct at least one static image.

In a case where the first and second main detectors 203 and 209 are positioned at a different portion, two static images having a different portion can be reconstructed.

In a case where the first and second main detectors 203 and 204 are positioned at the same portion, two static images having a different direction can be reconstructed.

(Two-detector opposite SPECT mode)

In this mode, as shown in FIGS. 31, 32, and 33, the first and second main detectors 203 and 209 are opposite to each other to sandwich the subject P therebetween. Also, the first line emitter 204 and the sub-detector 203 are opposite to each other to sandwich the subject P therebetween. In this case, the unnecessary second line emitter 210 is detached, or stored in a storage 222 as shown in FIG. 35. If the first line emitter 204 is unnecessary, the first line emitter 204 is detached, or stored in a storage 221 as shown in FIG. 34.

The first and second main detectors 203 and 209 are rotated from an initial state that they are opposite to each other at the same speed by the control of the controller 215. By this control, the first and second main detectors 203 and 209 rotate around the subject as being opposite to each other.

Moreover, the sliding of the first line emitter 204 and the sub-detector 205 is synchronized with the above rotation by the controller 215. For example, a rotation of 5° and a rotation stop for a predetermined period of time are alternatively repeated. During the rotation stopping period, the gamma rays from RIs provided onto the subject are continuously detected by the main detectors 203 and 209.

Also, during the rotation stopping period, the line emitter 204 and the sub-detector 205 slide from an end to an end of an effective visual field of the main detectors 203 and 209 (from and end to an end of a photographing portion of a heart, etc.) at a fixed speed. During a next rotation stopping period, the line emitter 204 and the sub-detector 205 inversely slide in the same distance at the same speed.

During the sliding, the gamma rays, which are emitted from the line emitter 204 and transmitted through the subject, are continuously detected by the sub-detector 205, so that the energy spectrums are acquired. Then, similar to the first embodiment, the absorption ratios are calculated based on the energy spectrum.

This absorption ratios is used in the absorption correction of the count values counted based on the outputs of the main detectors 203 and 209 obtained by the absorption corrector 218. Then, RIs distribution is reconstructed by the processor 219 based on the absorption-corrected count values.

(90° SPECT mode)

Next, in the 90° SPECT mode, as shown in FIGS. 36 to 38, the first detector 203 is shifted around the rotation axis at 90° against the second main detector 209. In this mode, since the sub-detector 205 is not used, the sub-detector 205 is detached or withdrawn.

The first and second main detectors 203 and 209 are rotated from an initial state that they are shifted at 90° at the same speed by the control of the controller 215. By this control, the first and second main detectors 203 and 209 rotate around the subject as being opposite to each other.

Moreover, the sliding of the first and second line emitters 204 and 210 is synchronized with the above rotation by the controller 215. For example, a rotation of 5° and a rotation stop for a predetermined period of time are alternatively repeated. During the rotation stopping period, the gamma rays from RIs provided onto the subject are continuously detected by the main detectors 203 and 209.

Also, during the rotation stopping period, the line emitters 204 and 210 slide from an end to an end of an effective visual field of the main detectors 203 and 209 (from and end to an end of a photographing portion of a heart, etc.) at a fixed speed. During a next rotation stopping period, the line emitters 204 and 210 inversely slide in the same distance at the same speed.

During the sliding, the gamma rays, which are emitted from the line emitters 204 and 210 and transmitted through the subject, are continuously detected by the main detectors 203 and 209.

In the absorption corrector 218, the outputs of the main detectors 203 and 209 are separated into a transmission component and RIs component based on the difference in the energy peak. Then, the absorption ratios are calculated based on the count values of the transmission component. Also, the count values of the RIs component are corrected based on the absorption ratios. The processor 219 reconstructs the RIs distribution based on the absorption-corrected count values.

In this mode, the gamma rays, which are from the line emitters 204 and 210, and the gamma rays, which are sent from the RIs given to the subject P, are detected by the same main detectors 203 and 209. Due to this, there is fear of crosstalk of both components. However, as explained in the first embodiment, the semiconductor elements have energy resolution twice or more as large as the normal anger-type detector. Moreover, the semiconductor elements have an extremely excellent count ratio characteristic of 500 Kcps or more. As a result, both components can be separated with high accuracy.

(One detector SPECT imaging mode)

In this mode, each of the first and second main detectors 203 and 209 is positioned at a different portion, and SPECT imaging is individually performed.

In this mode, it is only the first imaging system that can measure the absorption ratios in parallel with imaging and that can correct absorption. Since the second imaging system has no sub-detector, the second imaging system can neither measure the absorption ratios nor correct absorption ratios in parallel with imaging.

In this mode, for example, in the head portion, the absorption ratios is relatively uniform. Due to this, the second imaging system is used to photograph the head portion. Moreover, the first imaging system is used to photograph a portion to which a correct absorption-correction is needed, for example, a heart.

Thus, the gamma camera system of this embodiment can flexibly correspond to various kinds of imaging modes, and measure the absorption ratios with high accuracy in parallel with imaging.

(Third embodiment)

Figure 39:
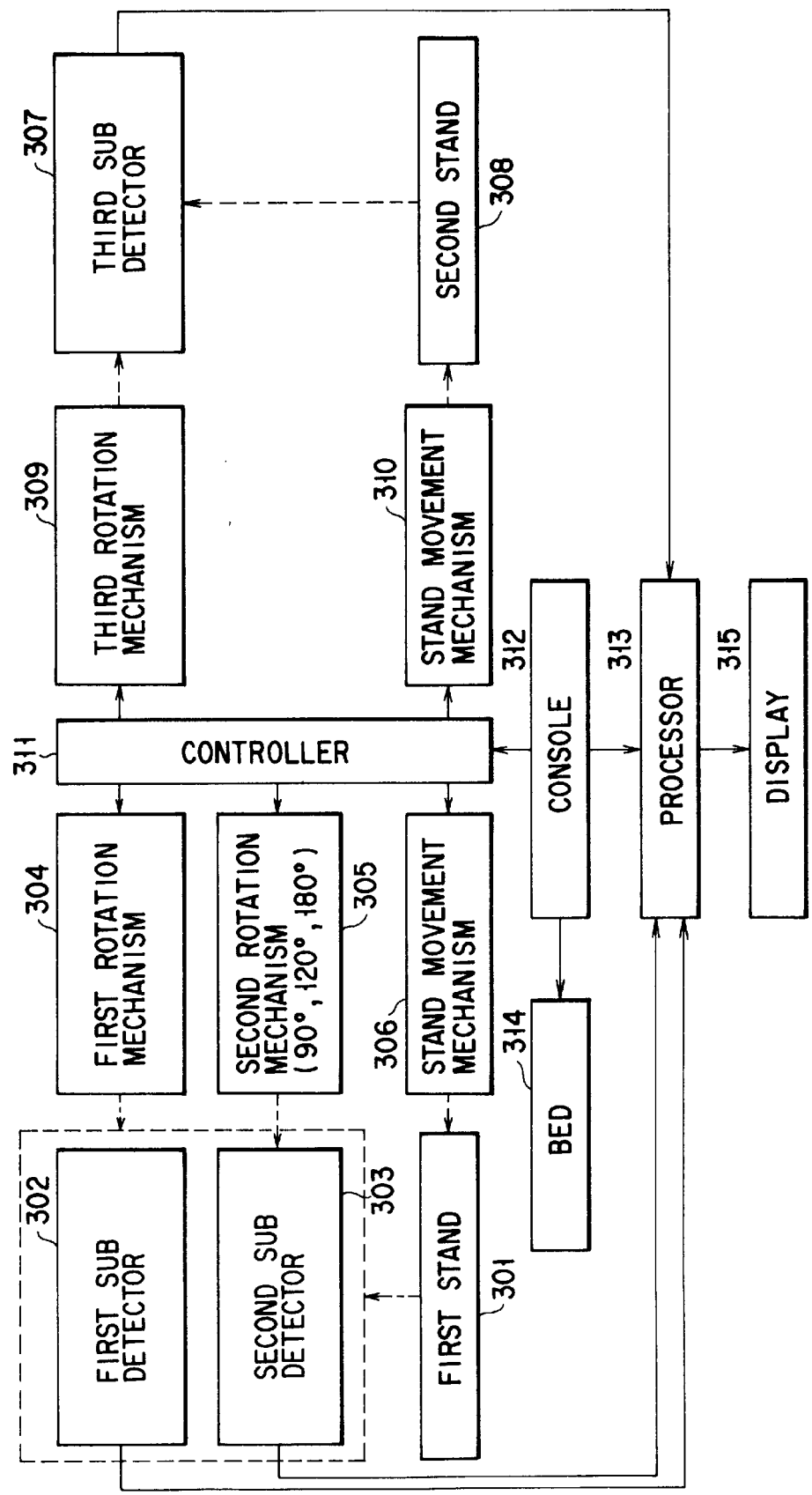
FIG. 39 is a block diagram showing the functions of the gamma camera system according to a third embodiment of the present invention.

FIG. 39 shows a block diagram of the gamma camera system of a third embodiment. FIG. 41 shows the side view of the gamma camera system. FIGS. 42 and 43 show front views of first and second imaging systems, respectively. An object of this embodiment is to provide a gamma camera system, which can flexibly correspond to various kinds of imaging modes. Due to this, the system of this embodiment comprises two imaging systems, which are physically separated from each other.

A first imaging system has first and second semiconductor detectors 302, and 303. The first and second semiconductor detector 302 and 303 are semiconductor detectors as shown in FIG. 40. Each of these semiconductor detectors comprises a semiconductor array 392, a collimator 391, a circuit board 393, and a lead shield 394. In the semiconductor array 392, a plurality of semiconductor elements (CdZnTe), which directly detect the gamma rays, are arrayed two-dimensionally. The collimator 391 limits the incident direction of the gamma rays to the semiconductor array 392. The circuit board 393 has a preamplifier, a read-out circuit, etc., mounted thereon. The lead shield 394 shields disturbance gamma rays.

The first semiconductor detector 303 is supported by a rotation ring 331 of a first stand 301 to be rotatable around the subject P mounted on a bed 314. The rotation axis of the rotation ring 331 is consistent with the Y-axis. The second semiconductor detector 303 is supported by a rotation ring 339 of the first stand 301 to be rotatable around the subject P mounted on the bed 314 independently of the first semiconductor detector 302. The rotation axis of the rotation ring 339 is also consistent with the Y-axis.

The first stand 301 is mounted on a rail 337 (stand movement mechanism 306) provided on a floor. The first stand 301 can be moved to be parallel with the Y-axis by the stand movement mechanism 306.

A first rotation mechanism 304 comprises the rotation ring 331, a stepping motor 334, a pulley 335, and a driving belt 333. A second rotation mechanism 305 is structured in the same manner as the first rotation mechanism 304.

A second imaging system has a third semiconductor detector 307. The third semiconductor detector 307 is also a semiconductor detector as shown in FIG. 40. The third semiconductor detector 307 is supported by a rotation ring 341 of a second stand 308 to be rotatable around the subject P mounted on a bed 314. The rotation axis of the rotation ring 341 is also consistent with the Y-axis.

The second stand 308 is mounted on a rail 337 shearing with the first stand 301. The second stand 308 can be moved to be parallel with the Y-axis by a stand movement mechanism 310.

A third rotation mechanism 309 comprises the rotation ring 341, a stepping motor 344, a pulley 335, and a driving belt 343.

A controller 311 relatively controls the rotation of the first detector 302, that of the second detector 303, and that of the third detector 307.

A processor 313 reconstructs at least one RIs distribution based on the outputs of the first, second and third semiconductor detectors 302, 303, and 307.

The gamma camera system of this embodiment can flexibly correspond to various kinds of imaging modes by variously combining three semiconductor detectors 302, 303, and 307. FIG. 44 shows an arrangement of the first and second detectors 302 and 303.

(Three-detector SPECT imaging)

In this mode, as shown in FIG. 45, three semiconductor detectors 302, 303, and 307 are arranged in a triangular form. Specifically, the second semiconductor detector 303 is shifted around the rotation axis at 120° against the first semiconductor detector 302. Then, the third detector 307 is shifted around the rotation axis at 240°.

Three detectors 302, 303, and 307 are rotated from an initial state that they are arranged in the triangular form at the same speed by the controller 311. By this control, these detectors rotate around the subject as being maintained in the triangular form.

For example, a rotation of 5° and a rotation stop for a predetermined period of time are alternatively repeated. During the rotation stopping period, the gamma rays from RIs provided onto the subject are continuously detected by these three detectors 302, 303, and 307. The processor 313 reconstructs the RIs distribution based on the outputs of the first, second and third detectors 302, 303, and 307.

(Two-detector SPECT imaging)

In this mode, the second semiconductor detector 303 is shifted around the rotation axis at 90° or 180° against the first semiconductor detector 302.

Two detectors 302 and 303 are rotated from an initial state that they are shifted at 90° or 180° at the same speed by the controller 311. By this control, these detectors rotate around the subject as being maintained in the initial state.

For example, a rotation of 5° and a rotation stop for a predetermined period of time are alternatively repeated. During the rotation stopping period, the gamma rays from RIs provided onto the subject are continuously detected by these two detectors 302 and 303. The processor 313 reconstructs the RIs distribution based on the outputs of two detectors 302 and 303.

Moreover, in this mode, SPECT image of the other portion or the static image can be obtained by the third semiconductor detector 307. In other words, the processor 313 reconstructs SPECT image or the static image based on the output of the third detector 307.

(Static image)

In this mode, at least one static image is reconstructed by at least one of three semiconductor detectors 302, 303, and 307.

In a case where the first and third semiconductor detectors 302 and 307 are used, two static images having a different portion can be reconstructed.

In a case where the first and second semiconductor detectors 302 and 303 are used, two static images having a different direction of the same portion can be reconstructed.

In a case where the first, second third semiconductor detectors 302, 303, and 307 are used, two static images having a different direction of the same portion and the static image of the other portion can be reconstructed.

Thus, the gamma camera system of this embodiment can correspond to various kinds of image modes by freely combining three semiconductor detectors.

The structure in which the second semiconductor detector 303 is detachably set to the rotation ring 331 is used in this embodiment. The user first purchases the two-detector system. Thereafter, the user purchases only the second semiconductor detector 303 to add the two-detector system. Thereby, three-detector system can be easily obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed:

1. A gamma camera system comprising:
   a main detector for detecting gamma rays emitted from RIs injected into a subject;
   an emitter for emitting gamma rays to a subject;
   a sub-detector for detecting the gamma rays emitted from said emitter and transmitted through said subject, said sub-detector having at least one semiconductor element for directly detecting the gamma rays;
   a calculator for calculating an absorption ratio showing to what degree the gamma rays are absorbed in said subject based on an output of said sub-detector; and
   a processor for counting the number of gamma rays emitted from RIs injected into said subject to correct count values based on said absorption ratios and to reconstruct a RI-distribution based on the corrected count values;
   wherein said sub-detector and said emitter are arranged relative to said main detector such that an incident direction of gamma rays which can be detected by said sub-detector is different from an incident direction of gamma rays which can be detected by said main detector.

2. The gamma camera system according to claim 1, wherein said semiconductor element is CdZnTe.

3. The gamma camera system according to claim 1, wherein said sub-detector has a plurality of semiconductor elements arranged in a matrix form.

4. The gamma camera system according to claim 1, wherein said sub-detector has a plurality of semiconductor elements dispersively arranged.

5. The gamma camera system according to claim 1, wherein said main detector has a collimator for limiting an incident direction of said gamma rays, said emitter has a collimator for limiting a radiation direction of said gamma rays, said emitter is positioned at said main detector such that said radiation direction is substantially perpendicular to said incident direction to reduce a frequency of generation of an error in which said main detector detects the gamma rays emitted from said emitter.

6. The gamma camera system according to claim 1, wherein the gamma rays emitted from said emitter have peak energy different from the gamma rays emitted from said RIs, and said processor eliminates the error in which said main detector detects the gamma rays emitted from said emitter.

7. The gamma camera system according to claim 1, wherein said emitter is structured to selectively emit a plurality of kinds of gamma rays whose peak energy are different from each other.

8. The gamma camera system according to claim 7, wherein said emitter has first emitter elements for emitting gamma rays having first peak energy, and second emitter elements for emitting gamma rays having second peak energy.

9. The gamma camera system according to claim 1, further comprising a storage for storing said emitter, and said storage has a shield for shielding the gamma rays emitted from said emitter.

10. The gamma camera system according to claim 1, wherein said emitter has a cover for shielding the gamma rays emitted from said emitter.

11. The gamma camera system according to claim 1, wherein said processor is structured such that a tomographic image of the absorption ratios of the gamma rays can be reconstructed based on the output of said sub-detector.

12. The gamma camera system according to claim 1, further comprising means for acquiring an energy spectrum based on the output of said sub-detector, and means for analyzing said energy spectrum.

13. The gamma camera system according to claim 1, further comprising means for sliding said emitter and said sub-detector to scan said subject.

14. The gamma camera system according to claim 1, further comprising means for rotating said emitter and said sub-detector together with said main detector around said subject, and means for sliding said emitter and said sub-detector in synchronous with the rotation to scan said subject.

15. The gamma camera system according to claim 14, wherein said rotating means intermittently said main detector, said emitter and said sub-detector, said sliding means slides said emitter and said sub-detector during a stopping period of the rotation.

16. A gamma camera system comprising:

a first main detector for mainly detecting gamma rays emitted from RIs injected into a subject;

a first emitter for emitting gamma rays;

a sub-detector for detecting the gamma rays emitted from said first emitter and transmitted through said subject, said sub-detector having at least one semiconductor element for directly detecting the gamma rays;

a first stand for supporting said first main detector, said first emitter, and said sub-detector;

a second main detector for mainly detecting the gamma rays emitted from the RIs injected into the subject;

a second emitter for emitting gamma rays;

a second stand for supporting said second main detector, and said second emitter; and a processor for reconstructing at least one RI-distribution based on an output of said first main detector and an output of said second main detector;

wherein said sub-detector and said emitter are arranged relative to said first main detector such that an incident direction of gamma rays which can be detected by said sub-detector is different from an incident direction of gamma rays which can be detected by said first main detector.

17. The gamma camera system according to claim 16, wherein said first stand has a mechanism of rotating said first emitter and said first sub-detector together with said first main detector around a first rotation axis, and said second stand has a mechanism of rotating said second emitter together with said second main detector around a second rotation axis.

18. The gamma camera system according to claim 17, wherein said supported first emitter is shifted around said first rotation axis at substantially 90° against said supported first main detector, and said supported second emitter is shifted around said second rotation axis at substantially 270° against said supported second main detector.

19. The gamma camera system according to claim 16, further comprising means for automatically setting said first main detector and said second main detector to at least one of a first state that said first and second main detectors are opposite to each other and a second state that one of said first and second main detectors is shifted around said first or second rotation axis at substantially 90° against the other.

20. The gamma camera system according to claim 19, wherein when said first and second main detectors are set to said first or second state, said processor reconstructs one RI-distribution based on both outputs of said first and second main detectors.

21. The gamma camera system according to claim 19, wherein said processor reconstructs two RI-distributions by using the output of the first main detector and that of said second main detector, individually.

22. The gamma camera system according to claim 16, further comprising a calculator for calculating an absorption ratio showing to what degree the gamma rays are absorbed in said subject based on the output of said sub-detector, wherein said processor counts the number of the gamma rays emitted from said subject based on the output of said first main detector, and corrects the count values based on said absorption ratios, and reconstructs the RIs distribution based on the corrected count values.

23. The gamma camera system according to claim 16, further comprising a calculator for separating the signal components of the gamma rays emitted from said first and second emitters from the output of said first main detector and that of said second detector to calculate an absorption ratio show to what degree the gamma rays are absorbed based on the separated signal components when one of said first and second main detectors is shifted around said first or second rotation axis at substantially 90° against the other, said first and second emitters are opposite to each other, and said second main detector and said first emitter are opposite to each other, wherein said processor separates the signal components off the gamma rays emitted from said RIs from the output of said first main detector and that of said second main detector, and said processor counts the number of the gamma rays from said RIs based on the separated signal components, and said processor corrects the count values based on said absorption ratios to reconstruct the RIs distribution based on the corrected count values.

24. The gamma camera system according to claim 23, wherein the gamma rays emitted from said first and second emitter are different from the gamma rays emitted from said RIs in connection with peak energy, and said calculator separates signal components of the gamma rays emitted from said first and second emitters from the output of said first main detector and that of said second main detector, and said processor separates the signal components of the gamma rays sent from said RIs from the output of said first main detector and that of said second main detector.

25. The gamma camera system according to claim 16, wherein each of said first and second main detectors has a plurality of semiconductor elements for directly detecting the gamma rays, and said plurality of said semiconductor elements are arrayed in a matrix form.

26. The gamma camera system according to claim 16, further comprising a rail for sliding at least one of said first and second stands as the first rotation axis of said first stand and the second rotation axis of said second stand are maintained to be overlaid on each other.

27. The system according to claim 1, wherein the incident direction of gamma rays which can be detected by said sub-detector crosses orthogonally with the incident direction of gamma rays which can be detected by said main detector.

28. The system according to claim 1, wherein a detecting operation of said main detector and a detecting operation of said sub-detector are synchronized.

29. The system according to claim 1, further comprising a first main detector detecting gamma rays emitted from the RIs, said first main detector being mounted opposite to said second main detector.

* * * * *